United States Patent
Hoffman

(10) Patent No.: US 11,424,016 B1
(45) Date of Patent: Aug. 23, 2022

(54) PRODUCT ORDER DOSING FILLER SYSTEMS AND RELATED METHODS

(71) Applicant: Express Scripts Strategic Development, Inc., St. Louis, MO (US)

(72) Inventor: Robert E. Hoffman, Linden, IN (US)

(73) Assignee: Express Scripts Strategie Development, Inc., St. Louis, MO (US)

(*) Notice: Subject to any disclaimer, the term of this patent is extended or adjusted under 35 U.S.C. 154(b) by 455 days.

(21) Appl. No.: 16/540,404

(22) Filed: Aug. 14, 2019

Related U.S. Application Data

(60) Provisional application No. 62/765,071, filed on Aug. 17, 2018.

(51) Int. Cl.
  *G16H 20/13* (2018.01)
  *B65G 1/137* (2006.01)
  *G06K 7/14* (2006.01)

(52) U.S. Cl.
  CPC .......... *G16H 20/13* (2018.01); *B65G 1/1371* (2013.01); *G06K 7/1413* (2013.01)

(58) Field of Classification Search
  CPC .... G16H 20/13; G16H 20/10; G07F 17/0092; B65B 5/103; A61J 7/0069; A61J 7/0454; A61J 2205/30
  See application file for complete search history.

(56) References Cited

U.S. PATENT DOCUMENTS

| | | | |
|---|---|---|---|
| 5,988,858 A * | 11/1999 | Yuyama | B65G 1/1376 700/213 |
| 7,182,105 B1 * | 2/2007 | Feehan | G07F 17/0092 141/2 |
| 7,706,915 B2 | 4/2010 | Mohapatra | |
| 8,032,397 B2 | 10/2011 | Lawless | |
| 8,163,731 B2 | 4/2012 | Slater | |
| 8,215,540 B2 * | 7/2012 | Szesko | B65C 9/44 235/375 |
| 9,168,223 B2 | 10/2015 | Alfano | |
| 10,265,243 B2 | 4/2019 | Trower | |
| 10,322,066 B2 | 6/2019 | Thach | |
| 10,470,977 B2 | 11/2019 | Thach | |
| 2002/0066690 A1 | 6/2002 | Mattis | |
| 2004/0123564 A1 * | 7/2004 | McErlean | B65B 61/20 53/411 |
| 2004/0172169 A1 | 9/2004 | Curtis | |

(Continued)

*Primary Examiner* — Timothy R Waggoner
(74) *Attorney, Agent, or Firm* — Schwegman Lundberg & Woessner

(57) ABSTRACT

A method may include filling an order of a plurality of orders with a dosing filler system. The method may include receiving pharmaceutical orders including order for drugs used in multi-drug regimens using an order processing device. Each of the multi-drug regimen may have a plurality of scheduled dosing events. The method may include transporting containers to a dosing device, using the dosing device to dispense drugs for scheduled dosing events into the containers based on the received pharmaceutical orders, transporting the containers with the dispensed drugs to the container sealing device, using the container sealing device to seal the plurality of the containers with the dispensed drugs, transporting the dosage unit containers to the container identifier assembly, and using the container identifier assembly to identify the dosage unit containers based on the received pharmaceutical order.

20 Claims, 10 Drawing Sheets

(56) References Cited

U.S. PATENT DOCUMENTS

| | | |
|---|---|---|
| 2006/0086639 A1 | 4/2006 | Priebe |
| 2008/0312957 A1* | 12/2008 | Luciano, Jr. ....... B65D 75/5888 |
| | | 705/2 |
| 2011/0215007 A1* | 9/2011 | Wurtzel .................... B32B 7/10 |
| | | 206/204 |
| 2017/0029152 A1 | 2/2017 | Shim |
| 2019/0151196 A1 | 5/2019 | Trower |
| 2019/0326002 A1 | 10/2019 | Mould |

* cited by examiner

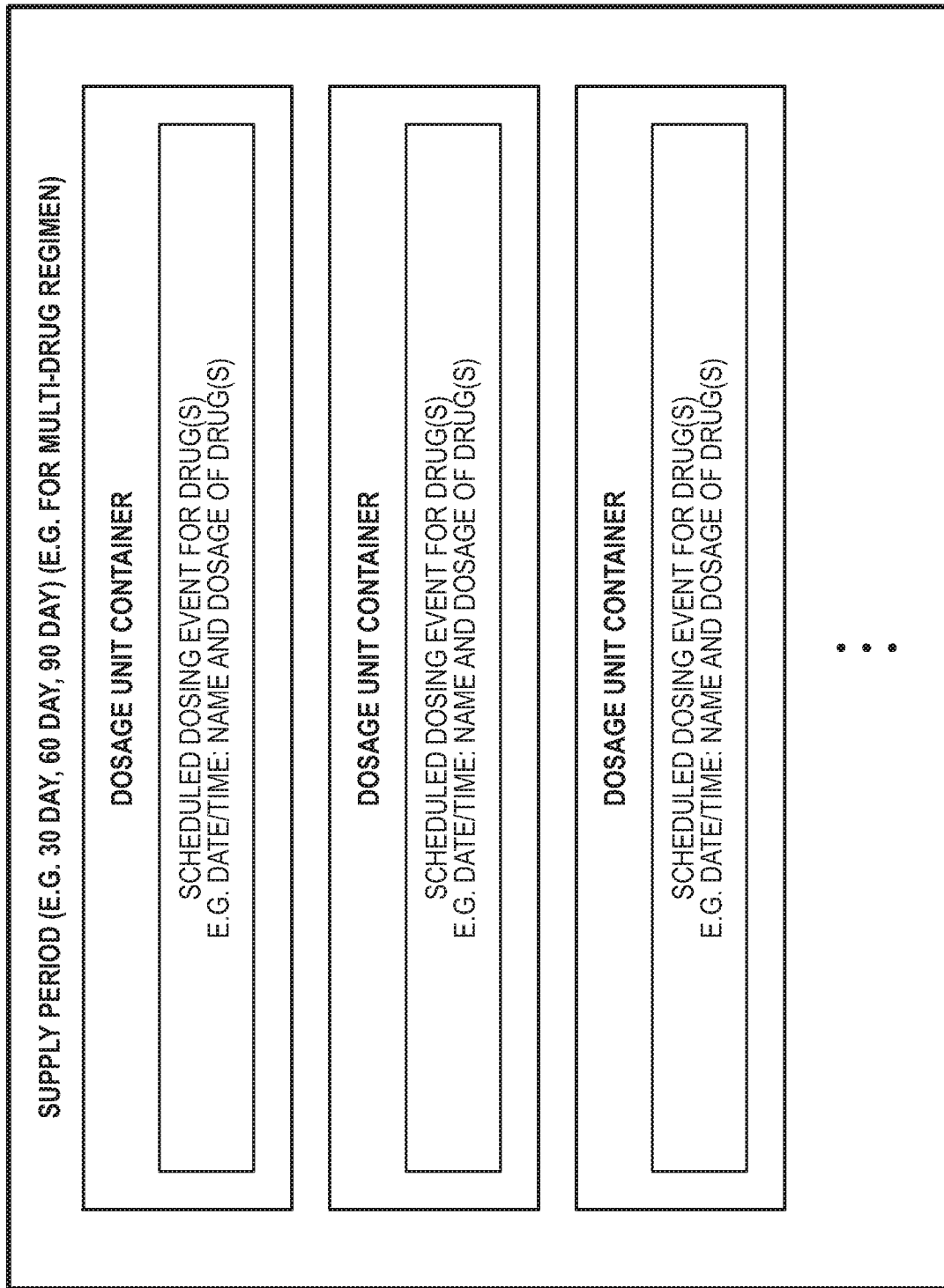

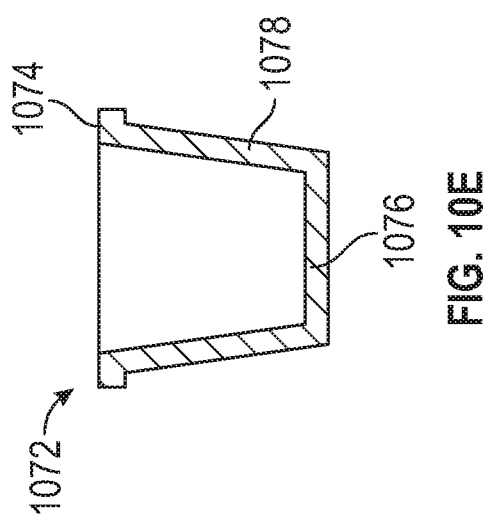
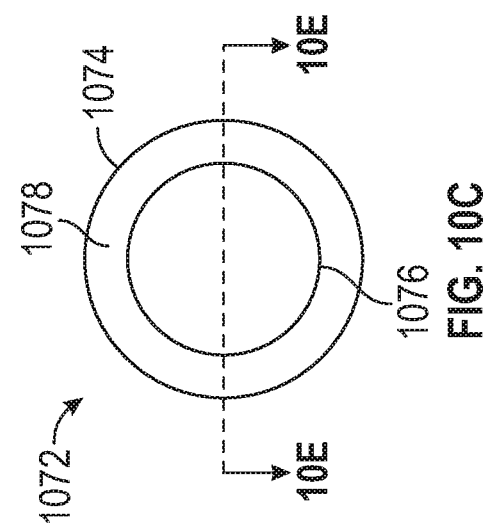
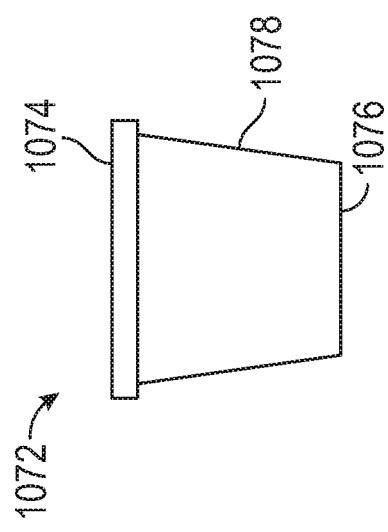
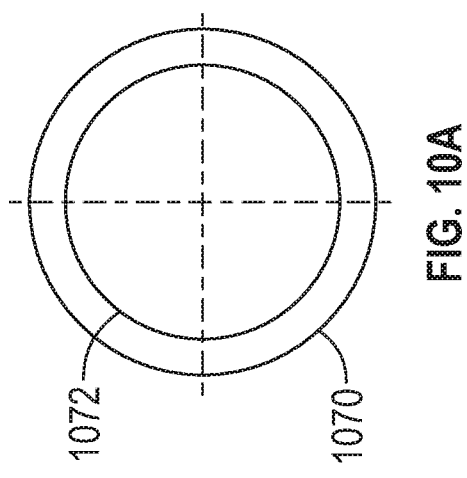
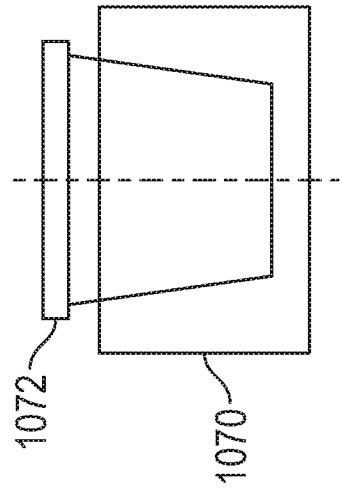

PRODUCT ORDER DOSING FILLER SYSTEMS AND RELATED METHODS

CLAIM OF PRIORITY

This application claims the benefit of priority under 35 U.S.C. § 119(e) of U.S. Provisional Patent Application Ser. No. 62/765,071, filed on Aug. 17, 2018, and titled "PRODUCT ORDER DOSING FILLER SYSTEMS AND RELATED METHODS", which is incorporated by reference herein in its entirety.

TECHNICAL FIELD

The present disclosure relates generally to automated filling centers such as a high-volume pharmacy, and more particularly, to systems, devices, and methods for filling daily dosage unit pharmacy orders of differing product selections within a high-volume pharmacy.

BACKGROUND

Pharmaceutical order processing systems typically involve labor intensive and/or complicated processes to sort and prepare portions of the order such that the various portions of the order may be correctly processed and/or joined up with other portions of the pharmacy order for packaging and shipment to the customer. Daily dosage unit pharmacy orders may include multiple separate daily dosage unit containers, each containing multiple pharmaceutical products to be taken by the customer at the same time. The pharmaceutical products of the daily dosage unit order or product selection are required to be dispensed accurately and in relatively small quantities to generate each of the daily dosage unit dosages, and thus the process for filling daily dosage unit orders is difficult to efficiently complete and requires substantial operator and machine time to ensure the dosages are correctly dispensed, packed, and shipped. Improved systems and methods for filling daily dosage unit pharmacy orders at a high volume to improve order fulfillment realization and customer satisfaction are needed.

This background section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

SUMMARY

This Summary includes examples that provide an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

An example of subject matter (such as a system, a device, apparatus or machine) may include an order processing device configured to receive pharmaceutical orders including orders for drugs used in multi-drug regimens. Each of the multi-drug regimens may have a plurality of scheduled dosing events. The subject matter may include a container transport system, and a container transfer device configured to transfer containers to the container transport system. The container transport system may be configured to transport the containers to a dosing device, a container sealing device, a container identifier assembly, and an inspection assembly. The dosing device may be configured to communicate with the order processing device and configured to dispense drugs for scheduled dosing times into the containers based on the received pharmaceutical orders. Each of the containers may correspond to a respective one of the plurality of scheduled dosing events. The container transport system may be configured to transport the containers with the dispensed drugs to the container sealing device. The container sealing device may be configured to seal to the plurality of the containers with the dispensed drugs. Each container may retain one or more drugs for one of the multi-drug regimens. Thus, each container may provide a dosage unit container corresponding to one of the plurality of scheduled dosing events for one of the multi-drug regimens. The container identifier assembly may be configured to identify the dosage unit containers based on the received pharmaceutical order. The inspection assembly may be configured to inspect each of the dosage unit containers.

An example of subject matter (e.g. a method, a means for performing acts, or a machine-readable medium including instructions that, when performed by the machine, cause the machine to perform acts) may include filling an order of a plurality of orders with a dosing filler system. The subject matter may include receiving pharmaceutical orders including order for drugs used in multi-drug regimens using an order processing device. Each of the multi-drug regimen has a plurality of scheduled dosing events. The subject matter may further include transferring containers to a container transport system, and transporting containers to a dosing device using the container transport system, and using the dosing device to dispense drugs for scheduled dosing events into the containers based on the received pharmaceutical orders. Each of the containers may correspond to a respective one of the plurality of scheduled dosing events. The subject matter may include transporting, using the container transport system, the containers with the dispensed drugs to the container sealing device, and using the container sealing device to seal the plurality of the containers with the dispensed drugs. Each container may retain one or more drugs for one of the multi-drug regimens. Thus, each container may provide a dosage unit container corresponding to one of the plurality of scheduled dosing events for one of the multi-drug regimens. The subject matter may include transporting, using the container transport system, the dosage unit containers to the container identifier assembly, and using the container identifier assembly to identify the dosage unit containers based on the received pharmaceutical order. The subject matter may include transporting, using the container transport system, the dosage unit containers to the inspection assembly, and using the inspection assembly to inspect each of the dosage unit containers.

An example of subject matter may include a drug package. The drug package may include drugs used in a multi-drug regimen having a plurality of scheduled dosing events. The drug package may include a plurality of dosage unit containers corresponding to the plurality of scheduled dosing events for the multi-drug regimen. Each of the plurality of dosage unit containers may contain one or more types of drugs for the multi-drug regimen, and each of the plurality of dosage unit containers may be constructed from a material to maintain a cup shape in an ambient environment and having a liner, such as an induction liner providing a hermetic seal that is tamper evident. Each of the dosage unit containers may be labeled with a corresponding one of the plurality of dosing times, and a name and a dosage for each of the one more types of drugs contained with the dosage unit container.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIG. 9 illustrates, by way of example and not limitation, a plurality of dosage unit containers that contain drug(s) for a scheduled dosing event for a supply period of a multi-drug regimen.

FIGS. 10A-10B illustrate, by way of example and not limitation, views of an example of a container within a puck; and FIGS. 10C-10E illustrate, by way of example and not limitation, an example of a container.

DETAILED DESCRIPTION

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Generally, a prescription order or pharmaceutical order may be generated for a high-volume pharmacy, where the prescription order may include more than one prescription drug for fulfillment. For example, the prescription order may include a single prescription drug. In another example, the prescription order may include two or more prescription drugs. Each prescription drug in a prescription order may be considered to be an order component of the prescription order. Pharmaceutical orders may include orders for drugs used in multi-drug regimens. Each of the multi-drug regimens has a plurality of scheduled dosing events. For example, a dosing event may be associated with a day and/or date, and time of the day (e.g. Monday, 8:00 AM; Monday, 8:00 PM) in which one or more of the drugs are administered. The order components may correspond to the scheduled dosing events. A quantity of a prescription drug (e.g. order component) may be distributed in pill bottles, containers, or other packaging. Multiple pharmaceutical products may also be dispensed together as part of a pharmaceutical product selection for a dosing event (e.g. daily dosage unit application of similar function). The multiple pharmaceutical products that make up a drug dose event or product selection may be dispensed into a containment object, which may be referred to as a dosage unit container, and then the containment object may be transported, inspected, and packed with multiple other containment objects also containing pharmaceutical product selections for daily dosage unit applications. It is noted that a pharmaceutical order may include, in addition to the drugs used in the multi-drug regimen, other non-prescription medicines or other products that are not medicinal such as, by way of example and not limitation, bandages. These other components of the pharmaceutical order may be packaged with the scheduled dosing events of the multi-drug regimen.

Figure 1:
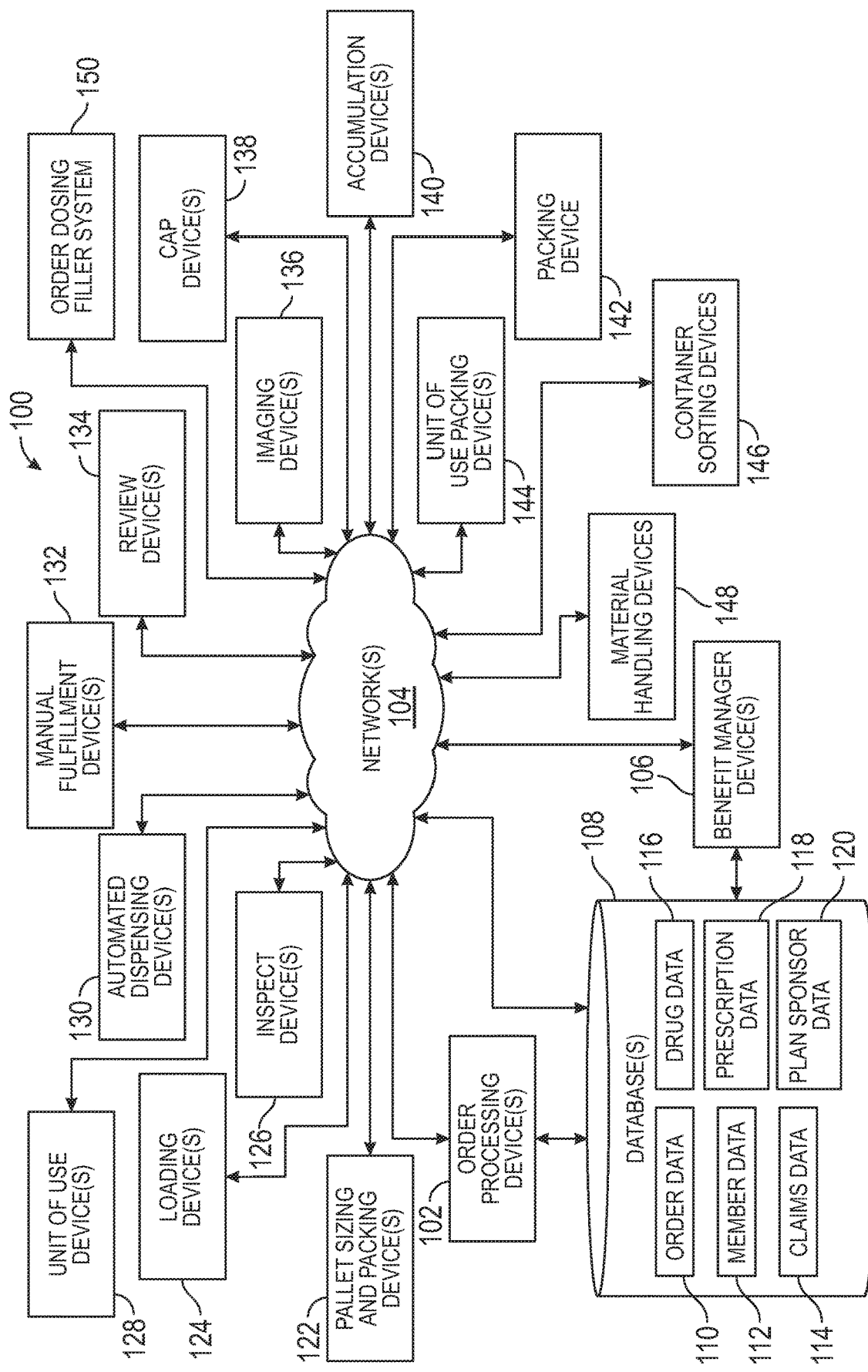
FIG. 1 illustrates, by way of example and not limitation, a block diagram of an embodiment of a pharmacy order processing system.

FIG. 1 illustrates, by way of example and not limitation, a block diagram of an embodiment of a pharmacy order processing system. While the system 100 is generally described as being deployed in a high-volume fulfillment center (e.g., a mail order pharmacy, a direct delivery pharmacy, a home delivery pharmacy and the like), the system 100 and/or components thereof may otherwise be deployed. The system 100 may include an order processing device 102 configured to communicate over a network 104 with a benefit manager device 106. Additional devices which may communicate over the network 104 with the benefit manager device 106 and/or the order processing device 102 may include at least some of: database(s) 108 which may store one or more than one of order data 110, member data 112, claims data 114, drug data 116, prescription data 118, and plan sponsor data 120; pallet sizing and pucking device(s) 122 (or other cart-like devices used to transport product); loading device(s) 124; inspect device(s) 126; unit-of-use device(s) 128; automated dispensing device(s) 130; manual fulfillment device(s) 132; review device(s) 134; imaging device(s) 136; cap device(s) 138; accumulation device(s) 140; packing device(s) 142; unit-of-use packing device(s) 144, container sorting device(s) 146 configured to image and sort containers, material handlings devices 148 configured to transport the containers throughout the system 100, and an order dosing filler system 150 configured to fill daily dosage unit pharmacy orders. The system 100 may also include additional devices.

The order processing device 102 may receive information about prescriptions being filled at a pharmacy in which the order processing device 102 is deployed. In general, the order processing device 102 may be a device located within or otherwise associated with a pharmacy location to enable fulfillment of a prescription by dispensing prescription drugs. In some embodiments, the order processing device 102 may be a device separate from a pharmacy that enables communication with other devices located within a pharmacy. For example, the order processing device 102 may be in communication with another order processing device 102 and/or other devices, such as other devices illustrated in FIG. 1, located with a pharmacy. In some embodiments, an external pharmacy order processing device 102 may have limited functionality (e.g., as operated by a patient requesting fulfillment of a prescription drug) when an internal pharmacy order processing device 102 may have greater functionality (e.g., as operated by a pharmacy).

The order processing device 102 may track a pharmaceutical order as it is fulfilled. A pharmaceutical order may include a prescription order for prescription medicine as well as may include non-prescription medicine and/or non-medical products. A prescription order may include one or more than one prescription to be filled by the pharmacy. The order processing device 102 may make pharmacy routing decisions and/or order consolidation decisions for a prescription order. The pharmacy routing decisions may include what device or devices in the pharmacy are responsible for filling at least a portion of the pharmaceutical order, where the order consolidation decisions include whether portions of a pharmaceutical order or multiple pharmaceutical orders should be shipped together for a patient or a patient family. The order processing device 102 may operate in combination with the benefit manager device 106.

Examples of the order processing device 102 may include a set-top box (STB), a receiver card, a mobile telephone, a personal digital assistant (PDA), a display device, a portable gaming unit, a tablet, and a computing system; however other devices may also be used. For example, the order processing device 102 may include a mobile electronic device, such an iPhone or iPad device by Apple, Inc., mobile electronic devices powered by ANDROID by Google, Inc., and a BLACKBERRY device by Blackberry Limited. The order processing device 102 may include other computing devices, such as desktop computing devices, notebook computing devices, netbook computing devices, gaming devices, and the like. The device 102 may include a processor, a memory to store data and instructions, and communication functionality. Other types of electronic devices that can use rules and instructions to execute various functions may also be used.

Examples of the network 104 include Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. The network 104 may include optical communications. The network 104 may be a local area network or a global communication network, such as the Internet. Other conventional and/or later developed wired and wireless networks may also be used. In some embodiments, the network 104 may include a prescribing network such as the electronic prescribing network operated by Surescripts of Arlington, Va.

The benefit manager device 106 may be operated by an entity at least partially responsible for creation and/or management of the pharmacy or drug benefit. The benefit manager operating the benefit manager device 106 may be a pharmacy benefit manager (PBM), or may be other entities that operate the benefit manager device 106 either on behalf of themselves, the PBM, or another entity. For example, the benefit manager may be operated by a health plan, a retail pharmacy chain, a drug wholesaler, a data analytics or other type of software-related company, or the like. In some embodiments, a PBM that provides the pharmacy benefit may also provide one or more than one additional benefits including a health benefit, a dental benefit, a vision benefit, a wellness benefit, a radiology benefit, a pet care benefit, an insurance benefit, a long term care benefit, a nursing home benefit, and the like. The PBM may, in addition to its PBM operations, operate one or more than one pharmacy. The pharmacies may be retail pharmacies, mail order pharmacies, etc.

By way of example and not limitation, a member (or a person on behalf of the member) of a pharmacy benefit plan administered by or through the PBM may attempt to obtain a prescription drug at a retail pharmacy location where the member can obtain drugs in a physical store from a pharmacist or pharmacist technician, or in some instances through mail order drug delivery from a mail order pharmacy location. The member may obtain a prescription drug directly or indirectly through the use of a machine, such as a kiosk, vending unit, mobile electronic device, or a different type of mechanical, electrical, an electronic communication device and/or computing device.

The member may have a co-pay for the prescription drug that reflects an amount of money that the member is responsible to pay the pharmacy for the prescription drug. The money paid by the member to the pharmacy may come from the personal funds of the member, a health savings account (HSA) of the member or the member's family, a health reimbursement arrangement (HRA) of the member or the member's family, a flexible spending accounts (FSA) of the member or the member's family, or the like. An employer of the member may directly or indirectly fund or reimburse the member or an account of the member for the co-pay.

The amount of the co-pay paid by the member may vary by the benefit plan of a plan sponsor or client with the PBM. The member's co-pay may be based on a flat co-pay (e.g., $10), co-insurance (e.g., 10%), and/or a deductible (e.g., for first $500 of annual prescription drug spend) for certain prescription drugs, certain types of prescription drugs, and/or all prescription drugs. In certain instances, the member may not pay the co-pay or may only pay for a portion of a co-pay for a prescription drug. For example, if the usual and customary cost for a generic version of a prescription drug is $4, and the member's flat co-pay is $20 for the prescription drug, the member may only pay $4 to receive the prescription drug. In another example involving a worker's compensation claim, no co-pay may be due by the member for the prescription drug. The co-pay may also vary based on the channel used to receive the prescription drug. For example, the co-pay for receiving prescription drugs from a mail order pharmacy location may be less than the co-pay for receiving prescription drugs from a retail pharmacy location.

In conjunction with receiving the co-pay (if any) from the member and dispensing the prescription drug to the member, the pharmacy submits a claim to the PBM for the prescription drug. The PBM may perform certain adjudication operations including verifying the eligibility of the member, reviewing the formulary of the member to determine appropriate co-pay, coinsurance, and deductible for the prescription drug, and performing a drug utilization review (DUR) on the member. The PBM then provides a response to the pharmacy following performance of at least some of the aforementioned operations. As part of the adjudication, the plan sponsor (or the PBM on behalf of the plan sponsor) ultimately reimburses the pharmacy for filling the prescription drug when the prescription drug was successfully adjudicated. The aforementioned adjudication operations generally occur before the co-pay is received and the prescription drug dispensed. However, the operations may occur simultaneously, substantially simultaneously, or in a different order. In addition, more or less adjudication operations may be performed as at least part of the adjudication process.

The amount of reimbursement paid to the pharmacy by a plan sponsor and/or money paid by the member may be based at least in part on the type of pharmacy network in which the pharmacy is included. Other factors may be used to determine the amount in addition to the type of pharmacy network. For example, if the member pays the pharmacy for the prescription without using the prescription drug benefit provided by the benefit manager, the amount of money paid by the member may be higher and the amount of money received by the pharmacy for dispensing the prescription drug and for the prescription drug itself may be higher. Some or all of the foregoing operations may be performed by executing instructions on the benefit manager device 106 and/or an additional device.

In some embodiments, at least some of the functionality of the order processing device 102 may be included in the benefit manager device 106. The order processing device 102 may be in a client-server relationship with the benefit manager device 106, a peer-to-peer relationship with the benefit manager device 106, or in a different type of relationship with the benefit manager device 106.

The order processing device 102 and/or the benefit manager device 106 may be in communication directly (e.g., through local storage) and/or through the network 104 (e.g., in a cloud configuration or software as a service) with a database 108 (e.g., as may be retained in memory or otherwise). The database 108 may store order data 110, member data 112, claims data 114, drug data 116, prescription data 118, and/or plan sponsor data 120. Other data may be stored in the database 108.

The order data 110 may include data related to the order of prescriptions including the type (e.g., drug name and strength) and quantity of each prescription in a prescription order. The order data 110 may also include data used for completion of the prescription, such as prescription materials. Prescription materials may be a type of order materials that include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, or the like. The order data 110 may be used by a high-volume fulfillment center to fulfill a pharmacy order.

In some embodiments, the order data 110 may include verification information associated with fulfillment of the prescription in the pharmacy. For example, the order data 110 may include videos and/or images taken of: the prescription drug prior to dispensing, during dispensing, and/or after dispensing; a prescription container (e.g., a prescription bottle and sealing lid) used to contain the prescription drug prior to dispensing, during dispensing, and/or after dispensing; the packaging and/or packaging materials used to ship or otherwise deliver the prescription drug prior to dispensing, during dispensing, and/or after dispensing; and/or the fulfillment process within the pharmacy. Other type of verification information such as bar code data read from pallets used to transport prescriptions within the pharmacy may also be stored as order data 110.

The member data 112 includes information regarding the members associated with the benefit manager. Examples of the member data 112 include name, address, telephone number, e-mail address, prescription drug history, and the like. The member data 112 may include a plan sponsor identifier that identifies the plan sponsor associated with the member and/or a member identifier that identifies the member to the plan sponsor. The member data 112 may include a member identifier that identifies the plan sponsor associated with the patient and/or a patient identifier that identifies the patient to the plan sponsor. The member data 112 may also include, by way of example, dispensation preferences such as type of label, type of cap, message preferences, language preferences, or the like.

The member data 112 may be accessed by various devices in the pharmacy, e.g., the high-volume fulfillment center, to obtain information utilized for fulfillment and shipping of prescription orders. In some embodiments, an external order processing device 102 operated by or on behalf of a member may have access to at least a portion of the member data 112 for review, verification, or other purposes.

In some embodiments, the member data 112 may include information for persons who are patients of the pharmacy but are not members in a benefit plan being provided by the benefit manager. For example, these patients may obtain drug directly from the pharmacy, through a private label service offered by the pharmacy, the high-volume fulfillment center, or otherwise. In general, the use of the terms member and patient may be used interchangeably herein.

The claims data 114 includes information regarding pharmacy claims adjudicated by the PBM under a drug benefit program provided by the PBM for one, or more than one, plan sponsors. In general, the claims data 114 includes an identification of the client that sponsors the drug benefit program under which the claim is made, and/or the member that purchased the prescription drug giving rise to the claim, the prescription drug that was filled by the pharmacy (e.g., the national drug code number), the dispensing date, generic indicator, GPI number, medication class, the cost of the prescription drug provided under the drug benefit program, the copay/coinsurance amount, rebate information, and/or member eligibility. Additional information may be included.

In some embodiments, other types of claims beyond prescription drug claims may be stored in the claims data 114. For example, medical claims, dental claims, wellness claims, or other type of health care-related claims for members may be stored as a portion of the claims data 114.

In some embodiments, the claims data 114 includes claims that identify the members with whom the claims are associated. In some embodiments, the claims data 114 includes claims that have been de-identified (e.g., associated with a unique identifier but not with a particular, identifiable member).

The drug data 116 may include drug name (e.g., technical name and/or common name), other names by which the drug is known by, active ingredients, an image of the drug (e.g., in pill form), and the like. The drug data 116 may include information associated with a single medication or multiple medications.

The prescription data 118 may include information regarding prescriptions that may be issued by prescribers on behalf of patients, who may be members of the drug benefit plan, for example to be filled by a pharmacy. Examples of the prescription data 118 include patient names, medication or treatment (such as lab tests), dosing information, and the like. The prescriptions may be electronic prescriptions, paper prescriptions that have been scanned, or otherwise. In some embodiments, the dosing information reflects a frequency of use (e.g., once a day, twice a day, before each meal, etc.) and a duration of use (e.g., a few days, a week, a few weeks, a month, etc.).

In some embodiments, the order data 110 may be linked to associated member data 112, claims data 114, drug data 116, and/or prescription data 118.

The plan sponsor data 120 includes information regarding the plan sponsors of the benefit manager. Examples of the plan sponsor data 120 include company name, company address, contact name, contact telephone number, contact e-mail address, and the like.

The order processing device 102 may direct at least some of the operations of the devices illustrated in FIG. 1. In some embodiments, operations performed by one of these devices may be performed sequentially, or in parallel with the operations of another device as may be coordinated by the order processing device 102. In some embodiments, the order processing device 102 tracks a prescription with the pharmacy based on operations performed by one or more of the devices illustrated in FIG. 1.

A material transport system or assembly may be used to transport product. For example, conveyors may include gravity conveyors or powered conveyors. Powered conveyors may include but are not limited chain-driven conveyors, pallet conveyors and servo-controlled conveyors. Intelligent conveyor systems may be designed to control the speed and/or direction of lines of article motion, and may allow individual articles to be inserted or removed from the line. Intelligent conveyor system may be designed to enable electronic movement control of individual transport mechanisms (e.g. pucks) for the product. For example, conveyor systems may be designed with one or more servo motors, controlled by a programmable servo controller, to electronically control movement of an individual puck. An example of an intelligent system may move individual carts, with or without a puck in or otherwise connected to the cart, along rails, under electronic control, in order to enable individual articles to be inserted and/or removed from line(s) of articles. Material transport systems may include a rotating structure with a periphery. Objects may be on a surface near the periphery such that they move as the structure rotates. Other material transport systems may be used. The material transport system may include combinations different types of material transport systems, such as a combination of two or more of a gravity conveyor, a power conveyor, and an intelligent conveyor.

In some embodiments, by way of example, the system 100 may transport product such as prescription drug containers (e.g., between or among devices, such as one of more devices illustrated in FIG. 1, in the high-volume fulfillment center) by use of pallets. The pallet sizing and pucking device 122 may configure pucks in a pallet. A pallet may be a transport structure for a number of the prescription containers 101, and may include a number of cavities. A puck may be placed in one or more than one of the cavities in a pallet by the pallet sizing and pucking device 122. A puck may include a receptacle sized and shaped to receive a prescription container 101. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 102 based on prescriptions which the order processing device 102 decides to launch. In general, prescription orders in the storage device 108 reside in one or more than one queues, and are generally launched in a first-in-first-out order. However, the order processing device 102 may use logic and a variety of factors to determine when and how prescriptions are to be launched. For example, some non-limiting factors which may alter the first-in-first-out order of launching prescriptions in a pharmacy include the age of the order, whether the order required an outreach to a physician or some other intervention, whether there are any performance guarantees with plan sponsors or members, the available inventory of a given pharmaceutical in view of existing prescriptions already launched which will require that pharmaceutical, the zip code to which the order will be shipped, the workload and volume of various parts of the pharmacy, whether valid paperwork for the order has been received, and/or similar orders for the same pharmaceutical that are already to be launched. The logic may be implemented directly in the pallet sizing and pucking device 122, in the order processing device 102, in both devices 102, 122, or otherwise. Once a prescription is set to be launched, a puck suitable for the appropriate size of container for that prescription may be positioned in a pallet by a robotic arm or pickers. The pallet sizing and pucking device 122 may launch a pallet once pucks have been configured in the pallet.

The loading device 124 may load prescription containers into the pucks on a pallet by a robotic arm, pick and place mechanism, or the like. In one embodiment, the loading device 108 has robotic arms or pickers to grasp a prescription container and move it to and from a pallet or a puck. The loading device 124 may also print a label which is appropriate for a container that is to be loaded onto the pallet, and apply the label to the container 101. The pallet may be located on a conveyor assembly during these operations, e.g., at the high-volume fulfillment center.

The inspect device 126 may verify that containers are correctly labeled and positioned on a material transport system. For example, the inspect device 126 may verify that containers in a pallet are in correct spots on the pallet. The inspect device 126 may scan the label on one or more than one container on the pallet. Labels of the containers may be scanned or imaged in full or in part by the inspect device 126. Such imaging may occur after the container has been lifted out of its puck by a robotic arm, picker, or the like, or may be otherwise scanned or imaged while retained in the puck. In some embodiments, images and/or video captured by the inspect device 126 may be stored in the database 108 as order data 110.

The unit-of-use device 128 may temporarily store, monitor, label and/or dispense unit-of-use products. In general, unit-of-use products are prescription drug products that may be delivered to a patient or member without being repackaged at the pharmacy. These products may include pills in a container 101, pills in a blister pack, inhalers, and the like. Prescription drug products dispensed by the unit-of-use device 128 in their original packaging may be packaged individually or collectively for shipping, or may be shipped in combination with other prescription drugs dispenses by other devices in the high-volume fulfillment center.

The automated dispensing device 130 may include one or more than one device that dispense prescription drugs or pharmaceuticals into prescription containers in accordance with one or multiple prescription orders. In general, the automated dispensing device 130 may include mechanical and electronic components with, in some embodiments, software and/or logic to facilitate pharmaceutical dispensing that would otherwise be performed in a manual fashion by a pharmacist and/or pharmacist technician. For example, the automated dispensing device 130 may include high volume fillers that fill a number of prescription drug types at a rapid rate and blister pack machines that dispense and pack drugs into a blister pack. Prescription drugs dispensed by the automated dispensing devices 130 may be packaged individually or collectively for shipping, or may be shipped in combination with other prescription drugs dispenses by other devices in the high-volume fulfillment center.

The manual fulfillment device 132 may provide for manually fulfillment of prescriptions. For example, the manual fulfillment device 132 may receive or obtain a container and enable fulfillment of the container by a pharmacist or pharmacy technician. In some embodiments, the manual fulfillment device 132 provides the filled container to another device in the system 100 to be joined with other containers in a prescription order for a patient or member. In general, a manual fulfillment may include operations at least partially performed by a pharmacist or pharmacy technician. For example, a person may retrieve a supply of the prescribed drug, may make an observation, may count out a prescribed quantity of drugs and place them into a prescription container 101, or the like. Some portions of the manual fulfillment process may be automated by use of a machine. For example, counting of capsules, tablets, or pills (types of drug delivery structures) may be at least partially automated (e.g., through use of a pill counter). Prescription drugs dispensed by the manual fulfillment device 132 may be packaged individually or collectively for shipping, or may be shipped in combination with other prescription drugs dispenses by other devices in the high-volume fulfillment center.

The review device 134 may process prescription containers to be reviewed by a pharmacist for proper pill count, exception handling, prescription verification, and the like. Fulfilled prescriptions may be manually reviewed and/or verified by a pharmacist, as may be required by state or local law. A pharmacist or other licensed pharmacy person who may dispense certain drugs in compliance with local and/or other laws may operate the review device 134 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been cancelled, containers with defects, and the like.

The imaging device 136 may image containers once they have been filled with pharmaceuticals. The imaging device 136 may measure the fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 102, and/or stored in the database 110 as part of the order data 110.

The cap device 138 may be used to cap or otherwise seal a prescription container 101. In some embodiments, the cap device 138 may secure a prescription container with a type of cap in accordance with a patient preference (e.g., a preference regarding child resistance), a plan sponsor preference, a prescriber preference, or the like. The cap device 138 may also etch a message into the cap, although this process may be performed by a subsequent device in the high-volume fulfillment center. The cap may include an induction liner. After the cap with the induction liner is placed on the container, an induction sealer may heat the induction liner such that the induction liner forms a tamper-evident seal over the container.

The accumulation device 140 may be used to accumulate containers, including one or more types of containers, of prescription drugs in a prescription order. The accumulation device 140 may accumulate prescription containers from various devices or areas of the pharmacy. For example, the accumulation device 140 may accumulate prescription containers from the unit-of-use device 128, the automated dispensing device 130, the manual fulfillment device 132, and the review device 134, at the high-volume fulfillment center. The accumulation device 140 may be used to group the prescription containers prior to shipment to the member or otherwise.

The packing device 142 may be configured to package a prescription order in preparation for shipping the order. For example, the packing device 142 may box, bag, or otherwise package the fulfilled prescription order for delivery. The packing device 142 may further place inserts into the packaging. For example, bulk prescription orders may be shipped in a box, while other prescription orders may be shipped in a bag which may be a wrap seal bag. The packing device 142 may label the box or bag with the address and a recipient's name. The packing device 142 may sort the box or bag for mailing in an efficient manner (e.g., sort by delivery address). The packing device 142 may include ice or temperature sensitive elements for prescriptions which are to be kept within a temperature range during shipping in order to retain efficacy or otherwise. The package may then be shipped through postal mail, through a mail order delivery service that ships via group and/or air (e.g., UPS, FedEx, or DHL), through delivery service, through a locker box at a shipping site (e.g., Amazon locker or a PO Box), or otherwise.

The unit-of-use packing device 144 may be configured to package a unit-of-use prescription order in preparation for shipping the order. The unit-of-use packing device 144 may include manual scanning of containers to be bagged for shipping to verify each container in the order.

The devices illustrated in FIG. 1 may be separate device or combined. When multiple devices are present, the multiple devices may be of the same device type or models or may be a different device type or model.

Moreover, the system 100 shows a single network 104; however, multiple networks can be used. The multiple networks may communicate in series with each other to link the devices or in parallel to link the devices. Multiple devices may share processing and/or memory resources. The devices may be located in the same area or in different locations. For example, the devices may be located in a building or set of adjoining buildings. They may be interconnected (e.g. by conveyors), networked, and/or otherwise in contact with one another or integrated with one another, e.g., at the high-volume fulfillment center. In addition, the functionality of a device may be split among a number of discrete devices and/or combined with other devices.

Figure 2:
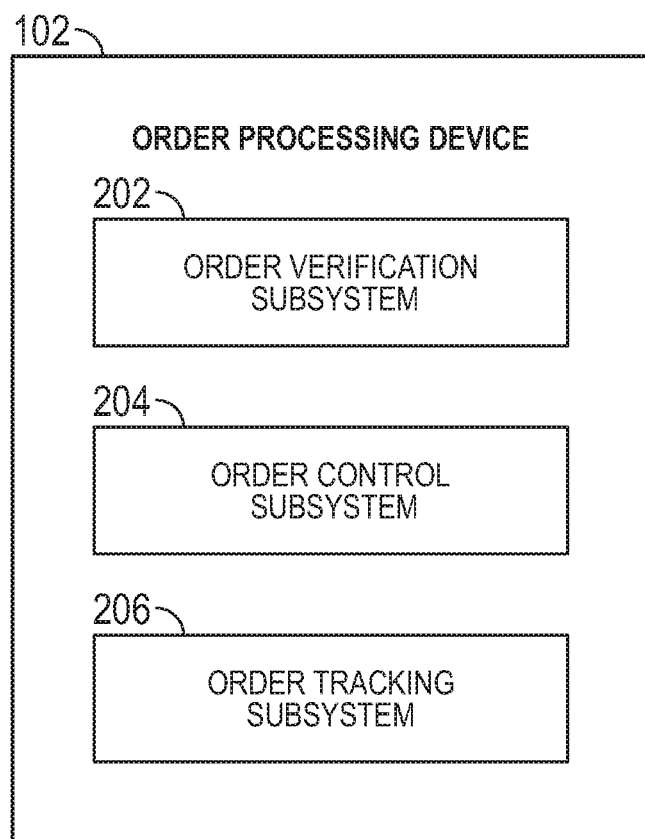
FIG. 2 illustrates, by way of example and not limitation, a block diagram of an embodiment of an order processing device that may be deployed within an order processing system such as the system of FIG. 1.

FIG. 2 illustrates, by way of example and not limitation, a block diagram of an embodiment of an order processing device that may be deployed within an order processing system such as the system of FIG. 1. The order processing device 102 may be used by one or more than one operator to generate pharmaceutical orders (e.g. prescription orders), make routing decisions, make order consolidation decisions, and/or view order status and other order related information. For example, the pharmaceutical order may be comprised of order components. The order processing device 102 may receive instructions to fulfill an order without operator intervention. An order component may include a prescription drug fulfilled by use of a container through the system 100. The order processing device 102 may direct an order component to the manual fulfillment device 132 and/or to the review device 134, and direct other components to the automated dispensing device 130. The order processing device 102 may direct the filling of an order component to be filled by the product selection order filling system 150. The order processing device 102 may direct order components to the accumulation device 140 for aggregation before shipping. The order processing device 102 may direct the order components directly to the packing device 142 if the prescription order does not require accumulation from various areas of the pharmacy for completion. The order processing device 102 may be deployed in the system 100, or may otherwise be used.

The order processing device 102 may include an order verification subsystem 202, an order control subsystem 204, and/or an order tracking subsystem 206. Other subsystems may also be included in the order processing device 102.

The order verification subsystem 202 may communicate with the benefit manager device 106 to, verify the eligibility of the member, review the formulary to determine appropriate co-pay, coinsurance, and deductible for the prescription drug, and/or perform a DUR. Other communications between the order verification subsystem 202 and the benefit manager device 106 may be performed for a variety of purposes.

The order control subsystem 204 controls various movements of the containers and/or pallets along with various filling functions during their progression through the system 100. The order control subsystem 204 may control filling of a plurality of individual doses for dosing events by the product selection order filling system 150. In some embodiments, the order control subsystem 204 may identify a prescribed drug in one or more than one prescription order as capable of being fulfilled by the automated dispensing device 130 or the automated per dosing event system 150. The order control subsystem 204 may determine which prescriptions are to be launched, and may determine that a pallet of automated-fill containers is to be launched. The order control subsystem 204 may determine that an automated-fill prescription of a specific pharmaceutical is to be launched, and may examine a queue of orders awaiting fulfillment for other prescription orders which will be filled with the same pharmaceutical. The order control subsystem 204 may then launch orders with similar automated-fill pharmaceutical needs together in a pallet to the automated dispensing device 130. As the devices may be interconnected by a system of one or more conveyors or other container movement systems, the order control subsystem 204 may control various conveyors to deliver the pallet from the loading device 124 to the manual fulfillment device 132, for example.

The order tracking subsystem 206 may track a prescription order as it progresses through (or stops at) various stations toward fulfillment. The order tracking subsystem 206 may track, record and/or update order history, order status or the like, e.g., the prescriptions filled by the system 150 and the automated dispensing devices 130. The order tracking subsystem 206 may store data locally (e.g., in a memory) or as a portion of the order data 110 stored in the storage device 108.

The order processing device 102 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The order processing device 102 may be utilized by the pharmacy to submit the claim to the PBM for adjudication.

Additionally, in some embodiments, the order processing device 102 may enable information exchange between the pharmacy and the PBM, for example, to allow the sharing of member information such as drug history, and the like, that may allow the pharmacy to better service a member (e.g., by providing more informed therapy consultation and drug interaction information, etc.). In some embodiments, the benefit manager device 106 may track prescription drug fulfillment and/or other information for patients that are not members or have not identified themselves as members, at the time (or in conjunction with the time) in which they seek to have a prescription filled at a pharmacy.

The order processing device 102 may also track and/or schedule literature or paperwork associated with each prescription order or multiple prescription orders that are being shipped together. The literature being tracked can be associated with a dosing event delivery from system 150 or the automated dispensing device 130.

The order processing device 102 may include circuitry, a processor, a memory to store data and instructions, and communication functionality. The order processing device 102 is dedicated to performing processes, methods and/or instructions described herein. Other types of electronic devices specifically configured to implement with the processes, methods and/or instructions described herein may also be used.

The storage device 108 may include: a non-transitory storage (e.g., memory, hard disk, CD-ROM, etc.) in communication with the benefit manager device 106, and/or the order processing device 102 directly and/or over the network 104. The non-transitory storage may store order data 110, member data 112, claims data 114, drug data 116, prescription data 118, and/or plan sponsor data 120. Further, the pharmacy order processing system 100 includes additional devices, including at least one container disassembly workstation 125, tray delivery conveyors 124, picking workstations 126, inspection workstations 130, packing delivery conveyors 132, packing workstations 134, and shipping conveyors 136, each additional device able to communicate with each other directly or over the network 104.

Figure 3:
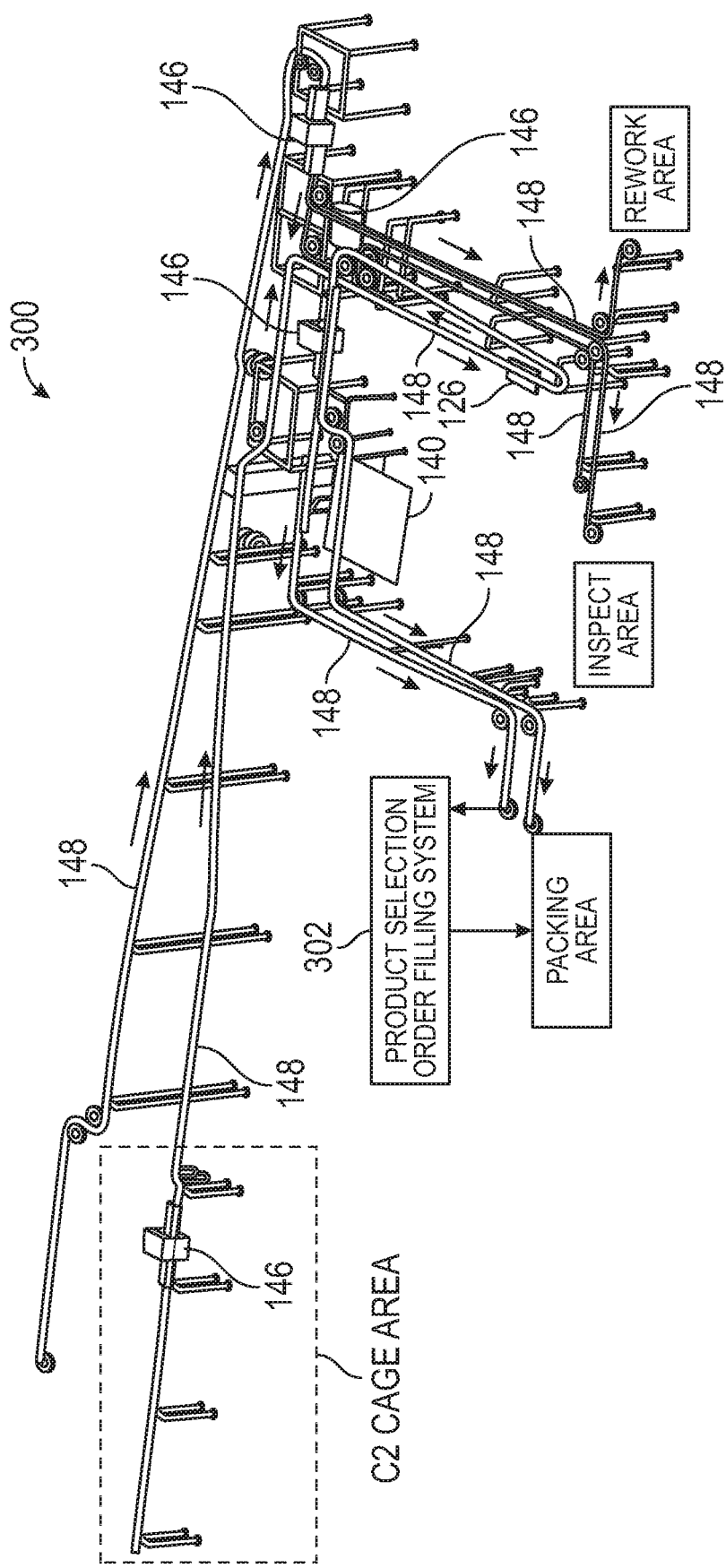
FIG. 3 illustrates, by way of example and not limitation, an embodiment of a product selection order filling system that may be deployed within a pharmacy order processing system such as the system of FIG. 1.

FIG. 3 illustrates, by way of example and not limitation, an embodiment of a product selection order filling system that may be deployed within a pharmacy order processing system such as the system of FIG. 1. The figure illustrates a "controls cage". In this embodiment, the controls cage is a more restricted or controlled-access portion of the pharmacy order processing system 100 separate from other portions of the pharmacy order processing system 100. The controls cage and be a separate room with a conveyor extending from the room. The controls cage can be metal or polymer enclosure surrounding a portion of the conveyor and other device to restrict access to the caged volume. The controls cage is adapted to rapidly process, at least a portion of pharmacy orders that include controlled substances having a C2, C3, C4, or C5 classification, in at least some cases from receipt of an order to shipping a packed filled order. In this embodiment, the controls cage is separate from the non-controlled substance portion of the pharmacy order processing system 100 and includes a separate C2 cage area for processing C2 substances. In other embodiments, the controls cage is substantially continuous with the non-controlled substance portion of the pharmacy order processing system 100.

In the example embodiment, the portion 300 of the pharmacy order processing system 100 illustrated in FIG. 3 includes an order dosing filler system 150, an accumulation device 140, an inspect device 126, four container sorting devices 146, a packing device 142, and multiple material handling devices 148 extending between at least one of the accumulation device 140, the inspect device 126, the container sorting devices 146, the packing device 142, a packing area, an inspect area, and a rework area. In this embodiment, the inspect device 126 is a scale configured to weigh the containers 101. In other embodiments, the controls cage includes any number of the order filling systems, the accumulation devices 140, the inspect devices 126, the container sorting devices 146, the packing device 142, and the material handling devices 148 arranged in any configuration that facilitates operation of the pharmacy order processing system 100 as described herein.

Figure 4:
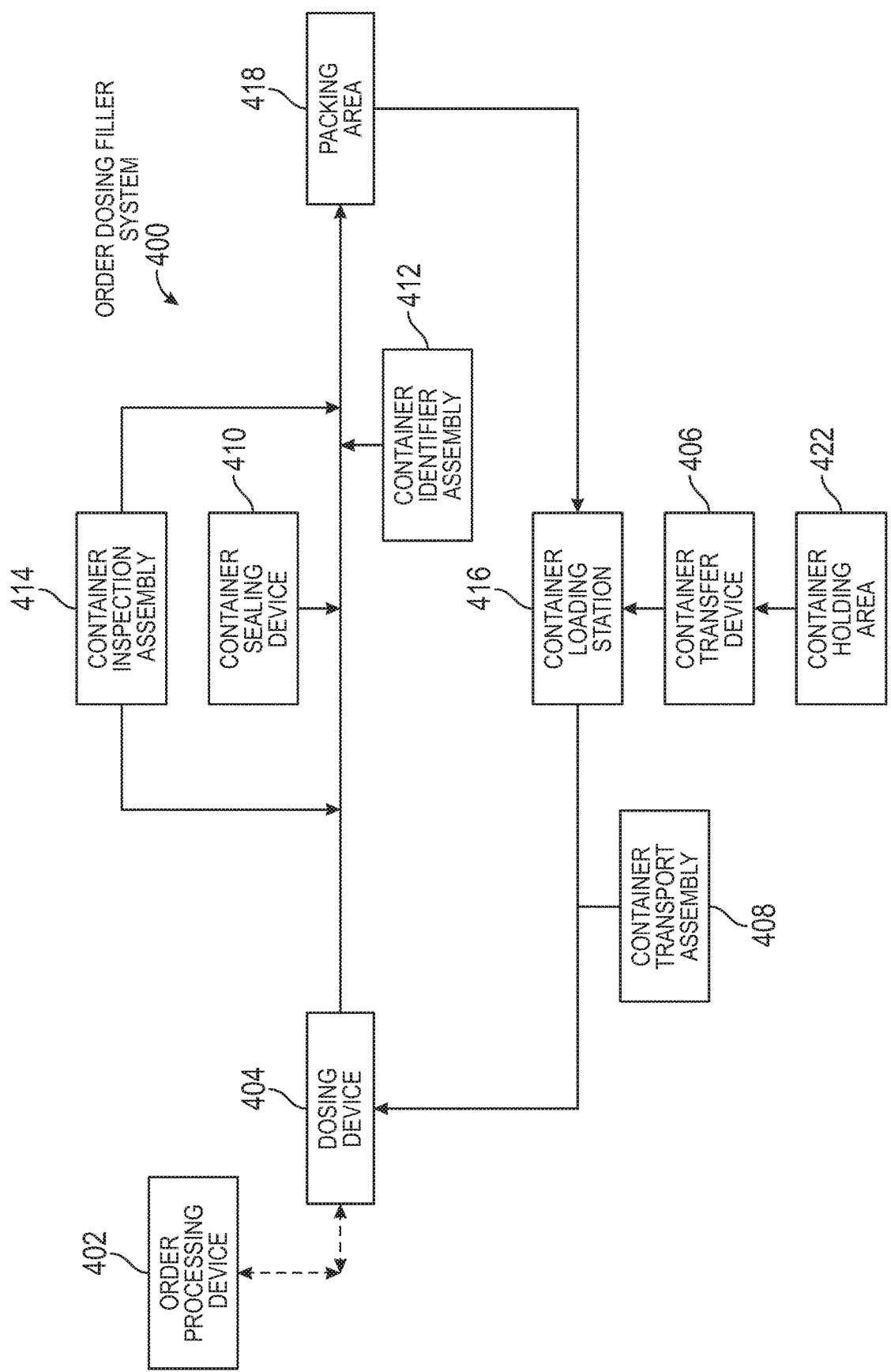
FIG. 4 illustrates, by way of example and not limitation, a process flow illustrating an embodiment of a method for filling an order of a plurality of orders with an order dosing filler system.

FIG. 4 illustrates, by way of example and not limitation, an embodiment of an order dosing filler system configured for filling at least a portion of a pharmaceutical order. In some embodiments, the order dosing filler system 400 may be used to create individually packaged containers of drugs of a single type or of multiple different types so that they may be conveniently taken by a person to whom the prescription drugs have been prescribed. The prescription drugs may be conveniently dispensed and packaged in a container with other prescription drugs, vitamins, other ingestibles, or the like. Additionally, the prescription drugs and other products contained within each container may be associated with a time and/or a day to reduce the chances of a patient forgetting to take their medications. For example, all of the drug structures to be consumed at a single dosing event can be packaged in a single container. Each dosing event may have its own unique container. In this embodiment, the order dosing filler system 400 may include an order processing device 402, a dosing device 404, container receptacles, a container transfer device 406, a container transport assembly 408, a container sealing device 410, a container identifier assembly 412, a container inspection assembly 414, a packing area 418, a container loading station 416, and a container holding area 422.

The order processing device 402 may be configured to receive orders for product selections and to communicate with the dosing device 404 that is connected to the order processing device 402. In some embodiments, the order reflects that instead of using a prescription bottle that retains a single type of prescription drug, multiple containers are used to retain one or multiple types of prescription drugs respectively in each container. In an example embodiment, each container is assigned to a single dosing event.

The dosing device 404 may be configured to dispense products in containers. The dosing device 404 may facilitate dispensing multiple different types of drugs (or other product) into a single container. By way of example, the dosing device 404 may dispense a first selection of products into a first set of containers and a second selection of the products into a second set of containers, wherein the first selection of the products represents a variety of the drugs and other products and the second selection represents another variety of the drugs and other products. In some embodiments, the dosing device 404 may include at least one dispensing and staging buffer tube extending from the dosing device 404 to at least one drop tube connected to at least one funnel. One or multiple dispensing and staging buffer tubes may be respectively extended to a drop tube connected to a funnel. Each of the dispensing and staging buffer tubes in this embodiment may be configured to facilitate transferring selection of products from the dosing device 404 to a drop tube. For example, when the dosing device 404 is providing dosing for two different types of products, at least one of the first selection of products and the second selection of products may be dispensed from the dosing device 404 to a drop tube. Each drop tube may be configured to facilitate receiving and transferring multiple and differing sizes and types of drugs and other products from the dosing device 404 to a funnel. The funnels may be used to facilitate guiding the multiple types of drugs and other products that make up each respective product selection into containers. Suitable containers may be sized similar to a single serve pod or container, such as pods used in coffee makers for making a single serving. The containers may be sized shorter than a standard pill bottle as the present containers store drugs for a single dosing event whereas a conventional pill bottle stores a single drug for an entire dosing schedule, e.g., 30, 60, 90 days. In some embodiments, the dosing device 404 may be configured to dispense any number of selections of the products that facilitates operation of the pharmacy order processing system 100 as described herein. Each of the first set of the containers may be configured to receive the first selection of the products, and each of the second set of the containers is configured to receive the second selection of the products based on the orders received from the order processing device 402. Example buffer tubes are shown in U.S. Pat. No. 9,697,335, which is incorporated herein by reference in its entirety.

The container receptacles may be configured to receive the first set of containers and the second set of the containers. More specifically, each container receptacle of the container receptacles may be configured such that it can receive one of the first set of the containers and one of the second set of the containers at a time without being reconfigured or otherwise modified. Additionally, each container may be configured to be received by one container receptacle of multiple container receptacle alignment apparatuses at each of the order processing device 402, the dosing device 404, the container transfer device 406, the container transport assembly 408, the container sealing device 410, the container identifier assembly 412, and the container inspection assembly 414. In some embodiments, each of the container receptacles may include a unique identifier configured to facilitate identification and tracking of each of the container receptacles during operation of the order dosing filler system 400. In some embodiments, each of the container receptacles may be marked with an identifier, such as an RFID tag or a printed identifier, for tracking purposes (e.g. tracking position and sequencing of pucks/containers).

The container transfer device 406 may be configured to selectively transfer the first set of the containers and the second set of the containers from a container holding area 422 to the container receptacles at a container loading station 416 based on the orders received by the order processing device 402. The container transfer device 406 may include a first set of gripper heads and a second set of the gripper heads. The first set of the gripper heads may be configured to grip and to release the first set of the containers. The second set of the gripper heads may be configured to grip and to release the second set of the containers. In an embodiment, each of the first set of the gripper heads and the second set of the gripper heads may include multiple suction cups configured to apply a vacuum to a portion of the containers such that the containers are retained along the gripper heads during transport. In some embodiments, each of the first set of the gripper heads and the second set of the gripper heads may include mechanical gripper heads configured to grip and retain the containers during transport of the containers by the first set of the gripper heads and the second set of the gripper heads.

The container transport assembly 408 assembly may include a conveyor. The conveyor may be configured to transport the container receptacles among the container loading station 416, the dosing device 404, and the packing area 418. In this embodiment, the packing area 418 may include a container unloading device configured to off-load the containers to a package to store multiple containers (e.g., a 14-day supply container, a 21-day supply container, a 30-day supply container, or the like). In some embodiments, the container receptacles may be connected to the conveyor. In some embodiments, the container receptacles may be placed on the conveyor by a container receptacle transfer device in a sequential order that correlates to the orders received by the order processing device. In some embodiments, the containers can be off-loaded to an automated bagging system for further processing and packaging, e.g., placed in a package or bag and then labelled for shipment. In some embodiments, the conveyor may include a substantially continuous loop. In some embodiments, the conveyor may include a linear section and return section to return the container receptacles to the container loading station 416.

The container sealing device 410 may be configured to seal each of the containers containing one of the first selection of the products and the second selection of the products such that each selection of the first selection of the products and the second selection of the products is retained within a respective one of the plurality of the containers. The sealing device may seal an inductive liner over the container to provide a tamper-evident seal. In one embodiment, the container sealing device may include a tunnel including a lidding device configured to apply lids to the containers. In other embodiments, the container sealing device may include lid manipulation device configured to connect "snap caps" to the plurality of the containers. In some embodiments, the container may have two or more different types of prescription drugs contained therein upon sealing.

In some embodiments, the container identifier assembly 412 may be configured to associate at least one identifier with each of the containers. The identifier may be used, for example, to identify prescription drugs contained there, a person to whom the prescription drug is prescriber, a date and time on which the person is to take the drugs, and the like. The identifier may also include the name of the pharmacy filling the container. In another example, the identifier includes the name of the prescriber. In some embodiments, the container identifier assembly 412 may include a bar code printer, a seal printer, and a medication identification printer. The bar code printer may be configured to associate a bar code with each of the containers. The bar code may be a 2D bar code, a 3D bar code, or otherwise. The seal printer may be configured to associate a timestamp with a seal of each of the containers. The medication identifier printer may be configured to associate a list of one of the first selection of the products and the second selection of the products on each of the containers based on the received orders associated with each of the containers. In some embodiments, the container identifier assembly 412 may be a laser printer, an ink-jet printer, a UV printer, a laser etching system, or the like. In some other embodiments, the container identifier assembly 412 may include an identifier device configured to associate a unique mark with each of the container receptacles.

The container identifier assembly 412 may be configured to inspect each of the containers. In some embodiments, multiple container sorting devices and multiple imaging devices may be used. By way of example, the container identifier assembly 412 may include a first container sorting device, a first imaging device, a second container sorting device, and a second imaging device. The first container sorting device may be configured to rotate each of the plurality of the containers containing one of the first selection of the products and the second selection of the products before each of the plurality of the containers is sealed. The first imaging device may be configured to image an interior of each of the containers to determine if one of the first selection of the products and the second selection of the products is present in each of the containers. In some embodiments, the first imaging device may include the comparison functionality to determine whether the selections are present. In some embodiments, the first imaging device communications with a different device to make the comparison and transmit a result of the comparison. The second container sorting device may be configured to rotate each of the plurality of the sealed containers and to divert sealed containers to the staging area if the sealed containers are part of a multiple container prescription order and the containers will be married together before packing and shipping. The second imaging device may be configured to image each of the plurality of the containers to determine if the container is sealed and to verify each of the bar codes associated with each of the plurality of the containers. In some embodiments, the second imaging device may be configured to image each container of the plurality of the containers to determine literature associated with each of the containers and an order. In this embodiment, the second imaging device may include at least one of a scanner and a barcode reader.

Figure 5:
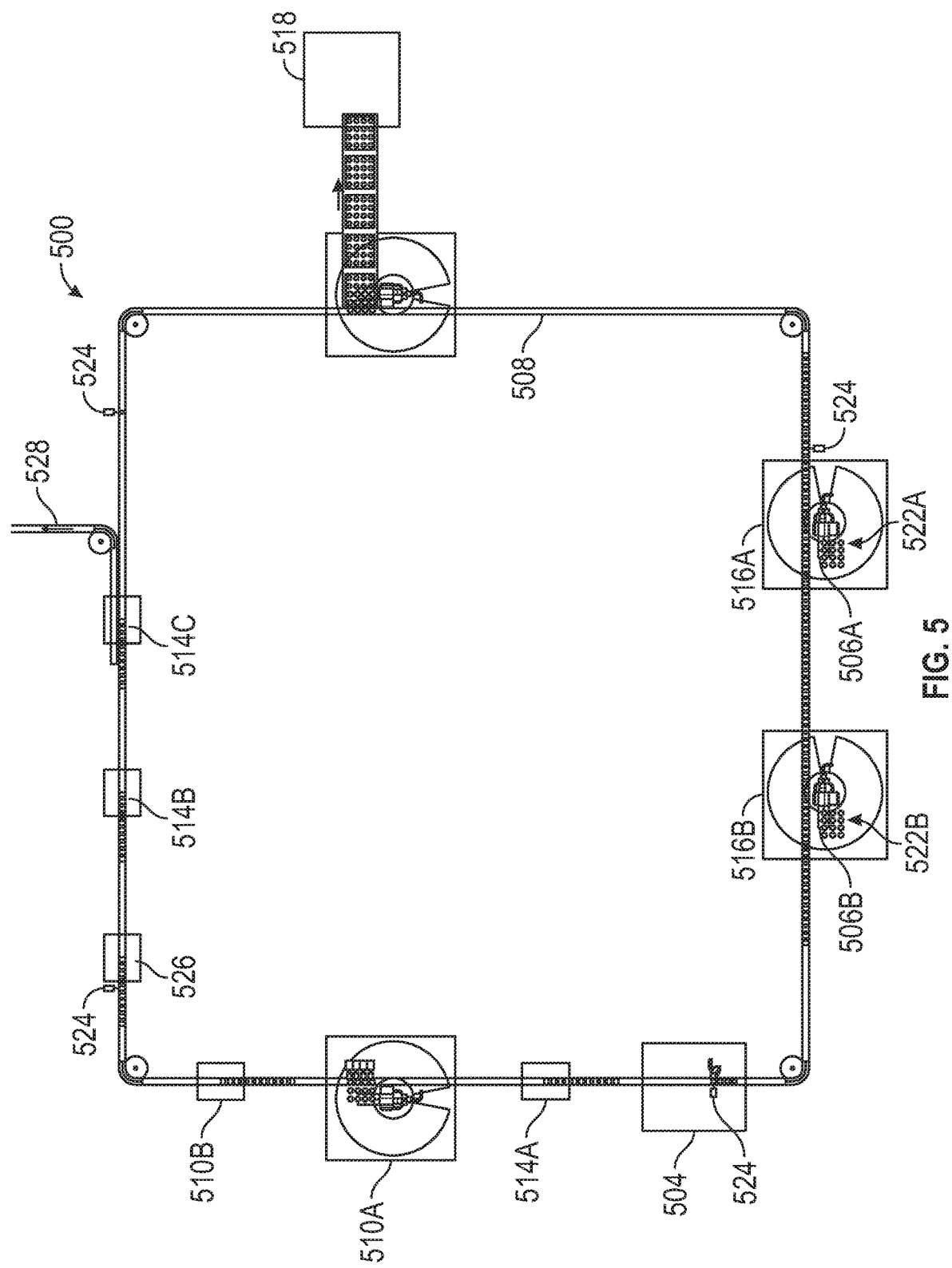
FIG. 5 illustrates, by way of example and not limitation, another example order dosing filler system according to another embodiment.

FIG. 5 illustrates, by way of example and not limitation, an embodiment of an order dosing filler system configured for filling at least a portion of a pharmaceutical order using cups to provide dosage unit containers that correspond to scheduled dosing events. The illustrated embodiment may be considered to be a more specific embodiment of the order dosing filler system 400 illustrated in FIG. 4. The illustrated order dosing filler system 500 in FIG. 5 includes a container transport assembly 508, which may be a conveyor system such as a vacuum conveyor. The system may transport pucks on the conveyor, where each puck is sized and configured to receive a cup for transport on the conveyor. For example, pallets with pucks in the pallets may be moved on the conveyor system.

Individual carts/pucks may be used to transport cups on the conveyor or rail. Intelligent conveyor systems may be designed to control the speed and/or direction of lines of article motion, and may allow individual cups to be inserted or removed from the line. Intelligent conveyor system may be designed to enable electronic movement control of individual transport mechanisms (e.g. pucks or carts with or without pucks) for the product. For example, conveyor systems may be designed with one or more servo motors, controlled by a programmable servo controller, to constant movement and control electronically of an individual puck. An example of an intelligent system may move individual carts along rails, under electronic control, in order to enable individual articles to be inserted and/or removed from line(s) of articles. Individual pucks may include a machine-readable identifier. Examples of machine-readable identifiers include, but are not limited to, bar codes, Quick Response (QR) codes, Radio Frequency Identification (RFID), Optical Character Recognition (OCR), and the like. The illustrated system includes puck bar code readers 524 positioned at different locations around the container transport assembly 508 used to identify the pucks as they are transported to the different stations along the conveyor. However, other machine-reading techniques may be used.

The system includes at least one cup load station for providing cups onto the container transport assembly 508. The illustrated system includes a small cup load station 516A and a large cup load station 516B. A cup magazine 522A and 522B (functioning as the container holding areas 422 illustrated in FIG. 4) and a suction cup pick head 506A and 506B (functioning as the container transfer device 406 in FIG. 4) are associated with each of the cup load stations 516A and 516B.

Some conveyors may constantly run such that it may be desirable to slow or stop pucks or other articles in position near stations along the conveyors. Crowders may be used to help control the flow of articles (e.g. pucks, cups, and the like) on the conveyor to allow a process to be performed on the article (e.g. fill cup, place a cap on the cup). A crowder may be a pneumatically operated bladder that opens up to stop or slow the article on the conveyor. The air can be cycled in slowly to slow the movement and control the stop.

The container for the pill(s) may have a variety of shapes (e.g. rectilinear or substantially rectilinear, cup-shaped, and the like). The cup-shaped container may have a generally circular foot print. Both the top and base of the cup may have a circular cross section. The base of the cup may have a smaller circular cross-section than the top of the cup. Some embodiments may use a cup where both the base and top have rectilinear cross-sections. The containers are configured to provide a volume within which the desired number of pills may be dispensed without excessive wasted volume. By way of example and not limitation, the approximate dimensions of the cup may be 1.25 to 1.5 inches in diameter and 1-1.5 inches deep for the small cups and 1.5-2 inches in diameter and 2.25 inches deep for the large cups. For example, a small cup may be sized to hold one or two pills and a large cup may be sized to hold three or more pills. Each cup may correspond to a scheduled dosing event in a multi-drug regimen. Pucks may be configured to conform to the outer dimensions and add another inch or so. A soft pneumatic bladder around the outside of the puck to help cushion and control stops which may be useful in preventing crashes that could cause the contents of the cup to spill. The cups (or other containers) may be constructed using a rigid or semi-rigid material, such as various types of polymer or plastic, configured to maintain the form of the container (e.g. cup-shaped form) in an ambient environment on the container transfer device and in a package. By way of example, the material may include food packaging materials such as polyethylene. For example, the material may be made from recyclable polypropylene #5 plastic similar to a yogurt or butter container, or cellulose polypropylene. The material may be a multi-layer blend of polymers.

After being loaded onto the conveyor (e.g. loaded into a puck), the cups may be transported to the next station which is illustrated as the dosing device 504 which is configured to fill the cup with the pill(s) for the scheduled dosing event associated with the cup. A crowder may be used to hold the puck/cup in place for the pills to be dispensed via a buffer tube and funnel into the cup. Alternatively, by way of example and not limitation, the conveyor may be intermittently stopped or slowed to allow the cup to be filled. The spacing of the cups may be controlled so that a cup is next to each station when the motion stops. An intelligent transport system may be used to independently control motion of each cup to allow the cups to be filled. The intelligent transport system may track the location of each cup as it travels between stations on the conveyor. For example, the system may be designed to dispense pill(s) into a cup within a second.

A camera image station 514A, which may form part of the container inspection assembly 414 illustrated in FIG. 4, may be used to verify that the correct pills are dispensed into the correct cup for the scheduled dosing event. For example, a camera may be used to verify color, size and/or shape of the pill(s). An ultrasonic sensor may be used to provide ultrasonic imaging for verifying the contents of the cup.

The container sealing device 410 illustrated in FIG. 4 may include a snap cap applicator 510A configured to snap a cap, which may be stored in a magazine of caps, onto the cup. A crowder may be used to hold the puck/cup in place for the cap to be attached. The cap may include liner on the inside of the cap. The liner may be configured to provide a tamper evident seal. In some embodiments the cap may include an induction liner on the inside of the cap. By way of example and not limitation, the induction liner may include a foil such as aluminum along with other coatings such as paper, wax and polymer. The cap or liner may include a metal/polymer laminate structure. The induction liner forms a tamper evident, hermetic seal with the cup as it travels through the induction tunnel 510B. The sealed cup may be labeled at 526 with identification information for the scheduled dosing event. For example, the identification information may include at least some of a date and/or day, a time, a list of medicines within the container, dosage of medicine, and a patient name. Other tamper-evident cap seals may be used.

The container inspection assembly 414 illustrated in FIG. 4 may further include a vision inspection station 514B to verify the sealed cup and a spin scan station 514C to determine if the cup should be accumulated (via an accumulation area 528) with other cups, product or literature before being packaged for shipment to the patient, or if the cups can continue to be transported to the packing area 518 (e.g. bagger), which may be used to package a 14, 21 or 30 day supply of medicine.

Figure 6:
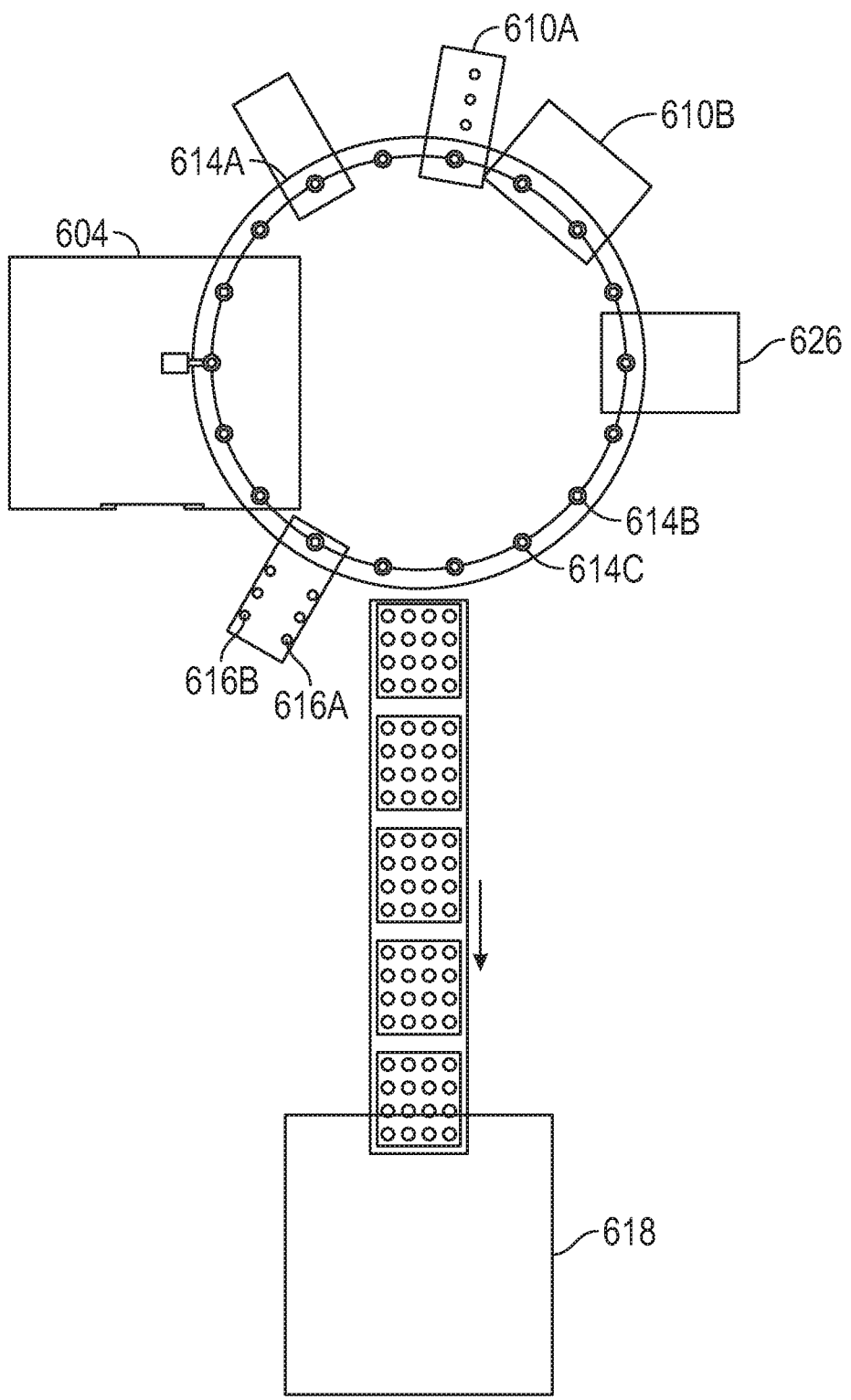
FIG. 6 illustrates, by way of example and not limitation, an embodiment of an order dosing filler system configured for filling at least a portion of a pharmaceutical order using cups to provide dosage unit containers that correspond to scheduled dosing events.

FIG. 6 illustrates, by way of example and not limitation, an embodiment of an order dosing filler system configured for filling at least a portion of a pharmaceutical order using cups to provide dosage unit containers that correspond to scheduled dosing events. The illustrated embodiment may be considered to be a more specific embodiment of the order dosing filler system 400 illustrated in FIG. 4. The illustrated order dosing filler system 600 in FIG. 6 includes a container transport system 608 includes a structure configured to rotate about a vertical axis, wherein the structure has a surface upon which a number of the plurality of containers (e.g. cups) may be positioned and transported as the structure rotates about the vertical axis. The structure may be referred to as a dial machine, an indexer or a rotary assembly table. The dial or wheel may be made of metal, and may have a spot cut out in which a cup may be placed, allowing the cups to go from point-to-point or station-to station. For example, the structure may be configured to rotate in the clockwise direction. By way of example and not limitation, the motion may be may be intermittent (e.g. under servo control) so that the cups stop for a moment at each station. The spacing of the cups may be controlled so that a cup is next to each station when the motion of the structure stops. The speed of rotation may be determined by the speed of the slowest station (e.g. about 1 second for filling cups with medicine). Similar to the system of FIG. 5, the system of FIG. 6 may include bar code readers (or other mechanisms for machine reading the articles (e.g. pucks) as they are transported among the stations.

The system includes at least one cup load station for providing cups onto the container transport assembly 608. The illustrated system includes a small cup load station 616A and a large cup load station 616B, which may be similar to the cup load stations in FIG. 5

After being loaded onto the container transport system (e.g. dial machine, indexer or rotary assembly table), the cups may be transported to the next station which is illustrated as the dosing device 604 which is configured to fill the cup with the pill(s) for the scheduled dosing event associated with the cup. For example, the system may be designed to dispense pill(s) into a cup within a second. A camera image station 614A, which may form part of the container inspection assembly 414 illustrated in FIG. 4, may be used to verify that the correct pills are dispensed into the correct cup for the scheduled dosing event. For example, a camera may be used to verify color, size and/or shape of the pill(s). An ultrasonic sensor may be used to verify the contents of the cup. In an example, the contents of the cups can be verified using the methods and structures described in U.S. Pat. No. 10,151,735, titled Solid Contents Verification Systems and Methods, which is hereby incorporated by reference.

The container sealing device 410 illustrated in FIG. 4 may include a snap cap applicator 610A configured to snap a cap, which may be stored in a magazine of caps, onto the cup. A crowder may be used to hold the puck/cup in place for the cap to be attached. The cap may include an induction liner on the inside of the lid. The induction liner forms a hermetic seal with the cup as it travels through the induction tunnel 610B. The sealed cup may be labeled at 626 with identification information for the scheduled dosing event. For example, the identification information may include at least some of a date and/or day, a time, a list of medicines within the container, and dosage of medicine. A patient name and/or prescription number may be included with the identification medication.

The container inspection assembly 414 illustrated in FIG. 4 may further include a vision inspection station 614B to verify the sealed cup and a scan station 614C to determine if the cup should be accumulated with other cups, product or literature before being packaged for shipment to the patient, or if the cups can continue to be transported to the packing area 618 (e.g. bagger), which may be used to package a 14, 21 or 30 day supply of medicine.

If there is an issue or problem with a particular container, the container may be sent to the accumulator for resolution. Also, the system may be configured so that if there in issue with an entire box, that entire box may be separated and sent to the QA conveyor for resolution. As shown, there are also several barcode readers to facilitate accurate dispensing.

These systems and processes are capable of providing a drug package for shipment. The drug package includes drugs used in a multi-drug regimen having a plurality of scheduled dosing events. The drug package includes a plurality of dosage unit containers corresponding to the plurality of scheduled dosing events for the multi-drug regimen. Each of the plurality of dosage unit containers contain one or more types of drugs for the multi-drug regimen. Each of the plurality of dosage unit containers are formed from a material to maintain a cup shape in an ambient environment and having an induction liner providing a hermetic seal that is tamper evident. Each of the dosage unit containers may be labeled with a corresponding one of the plurality of dosing times, and a name for each of the one more types of drugs contained with the dosage unit container. The label (or ink jet or laser printing) may also include a dosage for the drugs. Each of the dosage unit containers is labeled with a time-stamp indicative of a seal time.

Figure 7:
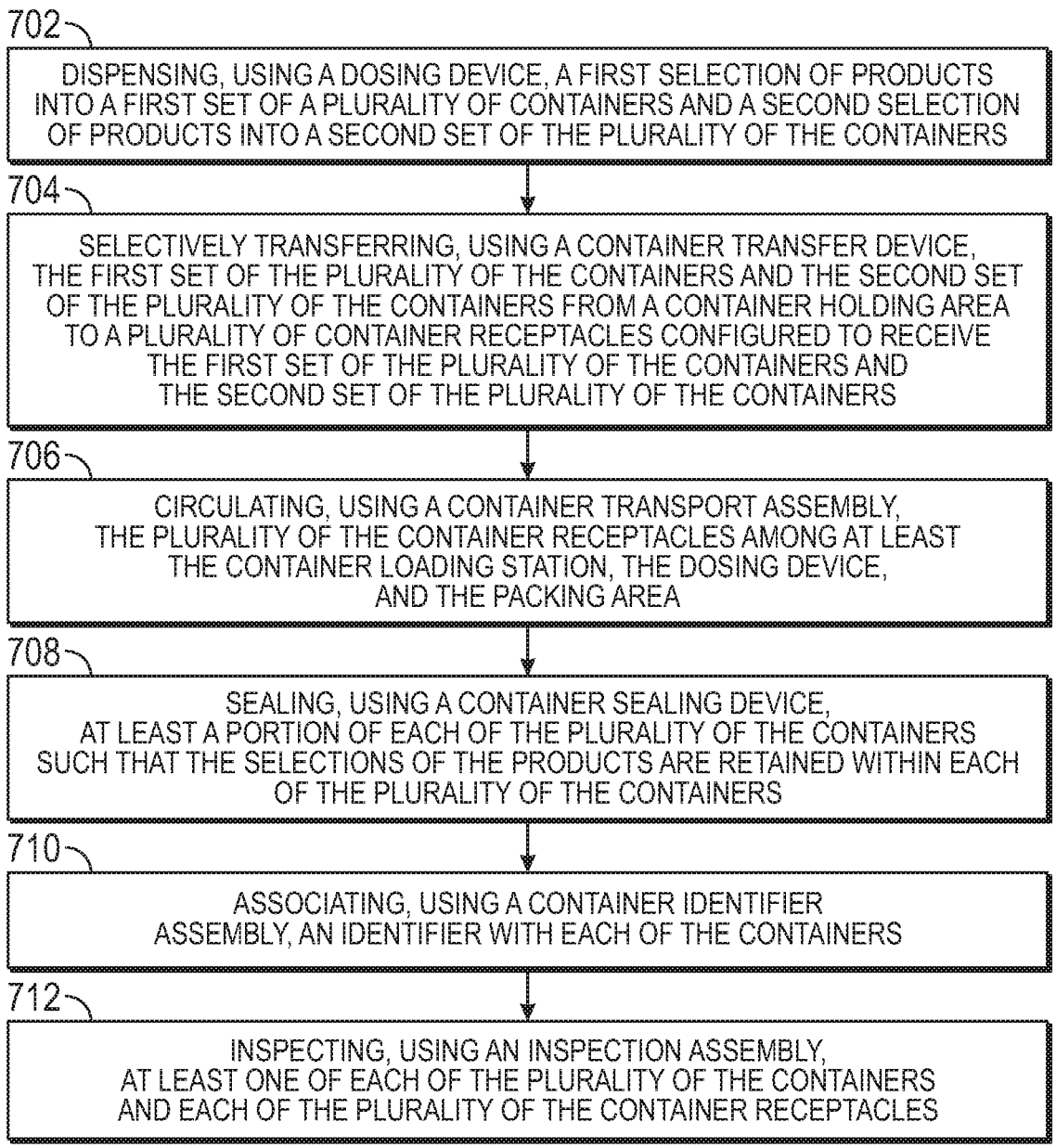
FIG. 7 illustrates a process flow of an embodiment of a method for filling at least a portion of a pharmaceutical order.

FIG. 7 illustrates a process flow of an embodiment of a method for filling at least a portion of a pharmaceutical order. At block 702, a first selection of products may be dispensed into a first set of containers and a second selection of the products are dispensed into a second set of the containers. In some embodiments, the containers may be configured at block 702 to receive respective product based on the received orders (e.g., by the order processing device 402). The operations performed at block 702 may be performed by the dosing device 404 or otherwise. The first set of the containers and the second set of the containers may be transferred at block 704 from a container holding area 422 to container receptacles at a container loading station based on the orders. The transfer may be performed by the container transfer device 406 or otherwise. In some embodiments, the container transfer device 406 may include a first set of gripper heads and a second set of gripper heads that are respectively configured to grip and to release the first set of the containers and the second set of the containers. At block 706, the container receptacles may be circulating among the container loading station 416, the dosing device 404 and the packing area 418 that includes a bagger device. The operations performed at block 706 may be performed by the container transport assembly 408, or may otherwise be performed. The container receptacles may be continuously circulated among the container loading station 416, the dosing device 404, and the packing area 418 along a circular path that enables the containers to be inserted and removed from the container receptacles at the desired locations without requiring an apparatus to reposition and/or re-stage the container receptacles for each cycle of each container receptacle. At block 708, the containers may be sealed such that the selections of the products are retained within each of the containers. The operations performed at block 708 may be performed by the container sealing device 410, or may otherwise be performed. An identifier may be associated with each of the containers at block 710. Each identifier may be associated with a container receptacle and may include a barcode affixed, etched, and/or otherwise applied to the container receptacle. The identifier may include information including container receptacle identifying information, prescription order information, patient information, and drug information, for example. The operations performed at block 710 may be performed using the container identifier assembly 412, or may otherwise be performed. At block 712, at least some of the containers and/or the container receptacles are inspected. The operations performed at block 712 may be performed using the container inspection assembly 414, or may otherwise be performed.

Figure 8:
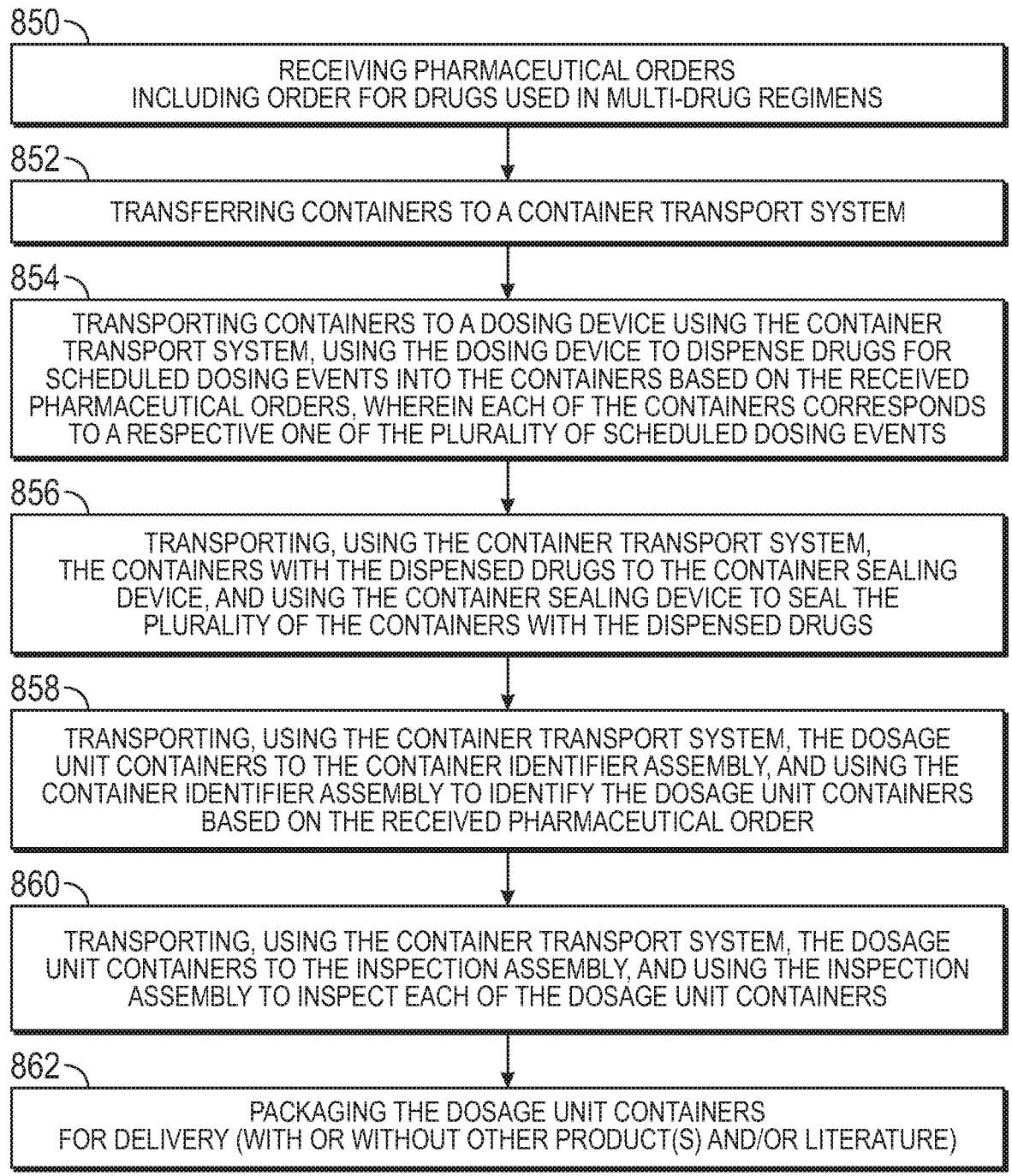
FIG. 8 illustrates a process flow of an embodiment of a method for filling at least a portion of a pharmaceutical order.

FIG. 8 illustrates a process flow of an embodiment of a method for filling at least a portion of a pharmaceutical order. At 850, pharmaceutical orders including order for drugs used in multi-drug regimens using an order processing device may be received. Each of the multi-drug regimen may have a plurality of scheduled dosing events. At 852, containers (e.g. cups) may be transferred to a container transport system. At 854, containers may be transported to a dosing device using the container transport system. The dosing device may be used to dispense drugs for scheduled dosing events into the containers based on the received pharmaceutical orders. Each of the containers corresponds to a respective one of the pluralities of scheduled dosing events. At 856, the containers with the dispensed drugs may be transported, using the container transport system, to the container sealing device, and using the container sealing device to seal the plurality of the containers with the dispensed drugs. Each container may retain one or more drugs for one of the multi-drug regimens. Each container may provide a dosage unit container corresponding to one of the plurality of scheduled dosing events for one of the multi-drug regimens. At 858, the dosage unit containers may be transported, using the container transport system, to the container identifier assembly. The container identifier assembly may be used to identify the dosage unit containers based on the received pharmaceutical order. At 860, the dosage unite containers may be transported, using the container transport system, to the inspection assembly. The inspection assembly may be used to inspect each of the dosage unit containers. At 862, the dosage unit containers may be packaged for delivery. The package (e.g. bag or box or other package) may include dosage unit containers for a supply period (e.g. 7-day supply, 14-day supply, 21-day supply, 30-day supply, 60-day supply, etc.). A supply period, by way of example and not limitation, may correspond to a time during which an amount of medicine can be taken as prescribed. Pharmacies may distribute prescribed medicine for a supply period. The package may include other products, such as but not limited to other prescription or non-prescription drugs, other health-care related products, or literature such as literature concerning the packaged drugs.

FIG. 9 illustrates, by way of example and not limitation, a plurality of dosage unit containers that contain drug(s) for a scheduled dosing event for a supply period of a multi-drug regimen. A multi-drug regimen may include at least two different types of drugs that are to be administered at different times over the course of a day. By way of example and not limitation, a first drug and second drug may be taken in the morning at breakfast, a third drug may be taken around noon, and the first and a fourth drug may be taken in the evening. This example has three scheduled dosing events (e.g. morning, noon and evening) per day. In another example, the dosing regimen may include one dosing event per day (or over another time period). Each dosing event may include one or more of the drugs used within the multi-drug regimen. Different dosing events may include different drug(s). The drug(s) for each dosing event may be within its own separate container, referred to herein as a dosage unit container. In an example, the dosage unit containers may be consecutively connected to the next container in a schedule of individual doses. A package may include the drugs ordered over the course of a supply period (e.g. 30-day supply of medicine, 60-day supply medicine or 90-day supply of medicine), and thus may include a corresponding number of the dosage unit containers over the course of the supply period.

FIGS. 10A-10B illustrate, by way of example and not limitation, views of an example of a container 1072 within a puck 1070; and FIGS. 10C-10E illustrate, by way of example and not limitation, an example of a container 1072. A puck 1070 may include a receptacle sized and shaped to receive a container 1072. Such containers 1072 may be supported by pucks 1070 during carriage in the pallet or other structure. Different pucks may have differently sized and shaped receptacles to accommodate containers of differing sizes, as may be appropriate for different prescriptions that may have different sized pill(s) for scheduled dosing events. In the illustrated embodiment, the puck 1070 has a receptacle that is sized and shaped to receive the bottom portion or base 1076 of the container (e.g. base with a circular footprint and walls from the base to a top where the top is a circular footprint larger than the base).

The illustrated container 1072 has an open top 1074 and a closed base 1076. The container may have a shape configured for nesting with other containers. For example, the base 1076 of the container 1072 may have a first dimension (e.g. circular footprint with a first diameter) and the top 1074 of the container 1072 may have a second dimension (e.g. circular foot print with a second diameter) that is larger than the base 1076. Thus, the containers may be stacked within each other, which may be a desirable characteristic for a container magazine designed to store containers and present containers for placement on a container transport system. The top of the illustrated container 1072 has a lip configured to cooperate with a snap cap such that the snap cap is able to snap onto the container. The container 1072 may have a sloping side wall 1078 extending from the base 1076 to the top 1074 of the container 1072. The sloping side wall 1078 may also be configured to enable the containers to nest within each other in a stacked configuration.

The containers 1072 may be configured to provide a volume within which the desired number of pills may be dispensed without excessive wasted volume. By way of example and not limitation, the approximate dimensions of the cup may be 1.25 to 1.5 inches in diameter and 1-1.5 inches deep for the small cups and 1.5-2 inches in diameter and 2.25 inches deep for the large cups. Cups may be designed with a volume to hold the pill(s) for a scheduled dosing event. For example, a small cup may be sized to hold one or two pills and a large cup may be sized to hold three or more pills. The resulting cup with the larger top 1074, smaller base 1076 and sloped side walls 1078 may be configured to nest within each other in a stack of cups. Each container (e.g. cup) may correspond to a scheduled dosing event in a multi-drug regimen. Pucks 1070 may be configured to conform to the outer dimensions and add another inch or so.

The cups (or other containers) may be constructed using a rigid or semi-rigid material, such as various types of polymer or plastic, configured to maintain the form of the container (e.g. cup-shaped form) in an ambient environment on the container transfer device and in a package. By way of example, the material may include food packaging materials such as polyethylene. For example, the material may be made from recyclable polypropylene #5 plastic similar to a yogurt or butter container, or cellulose polypropylene. The material may be a multi-layer blend of polymers. The thickness of the side walls 1078 may be designed, based on the material used to construct the container, to provide the desirable characteristics of the container. By way of example and not limitation, desirable characteristics may include one or more of the following: packaging safety for ingestibles (e.g. similar to food packaging safety), cost to manufacture, recyclability, and/or strength (e.g. strong enough to maintain the form of the container on the container transfer device or within packages during transit). A desirable characteristic may be to avoid an overly-strong container which may indicate wasted material. Thus, for example, the containers may be constructed to be weak enough for a person to easily squeeze the container in the person's hand to collapse the container, yet be strong enough to maintain the form of the container on the container transfer device or within packages during transit.

The container for the pill(s) may have a variety of shapes (e.g. rectilinear or substantially rectilinear shapes, cup-shaped including shapes with a circular bottom and a circular top, and the like). Both the top 1074 and the base 1076 of the container may have a similar shape. In some embodiments where the top and bottom have similar shapes, the top with the open end have a larger shape than the bottom with the closed end. For example, the cup-shaped container may have a generally circular foot print. Both the top and base of the cup may have a circular cross section, and the base of the cup may have a smaller circular cross-section than the top of the cup. Some embodiments may use a cup where both the base and top have rectilinear cross-sections.

In one aspect, the subject matter may provide an order dosing filler system that includes an order processing device to receive orders, a dosing device connected to the order processing device. The dosing device may be configured to dispense a first selection of products into a first set of a plurality of containers and a second selection of the products into a second set of the plurality of the containers. Each of the first set of the plurality of the containers may be configured to receive the first selection of the products and each of the second set of the plurality of the containers configured to receive the second selection of the products based on the received orders. The order dosing filler system may include a plurality of container receptacles configured to receive the first set of the plurality of the containers and the second set of the plurality of the containers, and may include a container transfer device configured to selectively transfer the first set of the plurality of the containers and the second set of the plurality of the containers from a container holding area to the container receptacles at a container loading station based on the orders. The container transfer device may include a first set of gripper heads and a second set of the gripper heads. The first set of the gripper heads may be configured to grip and to release the first set of the plurality of the containers. The second set of the gripper heads may be configured to grip and to release the second set of the plurality of the containers. The order dosing filler system may include a container transport assembly including a conveyor. The conveyor may be configured to circulate the plurality of the container receptacles among at least the container loading station, the dosing device, and a packing area including a bagger device. The order dosing filler system may include a container sealing device configured to seal to at least a portion of each of the plurality of the containers containing one of the first selection of the products and the second selection of the products such that each selection of the first selection of the products and the second selection of the products is retained within a respective one of the plurality of the containers. The order dosing filler system may include a container identifier assembly configured to associate at least one identifier with each of the plurality of the containers. The container identifier assembly may include a bar code printer configured to associate a bar code with each of the plurality of the containers, a seal printer configured to associate a timestamp with a seal of each of the plurality of the containers, and a medication identifier printer configured to associate a list of one of the first selection of the products and the second selection of the products on each of the plurality of the containers based on the received orders associated with each of the plurality of the containers. The order dosing filler system may include an inspection assembly configured to inspect each of the plurality of the containers. The inspection assembly may include a first container sorting device configured to at least one of rotate each of the plurality of the containers containing one of the first selection of the products and the second selection of the products before each of the plurality of the containers is sealed and divert at least one of the plurality of the containers to a separate staging area, an first imaging device configured to image an interior of each of the plurality of the containers to determine if one of the first selection of the products and the second selection of the products is present in each of the plurality of the containers, a second container sorting device configured to one of rotate each of the plurality of the sealed containers and divert at least one of the plurality of the sealed containers to the staging area, and a second imaging device configured to image each of the plurality of the containers to determine if the container is sealed and to verify each of the bar codes associated with each of the plurality of the containers. The second imaging device may include at least one of a scanner and a barcode reader.

In one aspect, the subject matter may provide an order dosing filler system that includes an order processing device to receive orders, and a dosing device connected to the order processing device and configured to dispense a first selection of products into a first set of a plurality of containers and a second selection of the products into a second set of the plurality of the containers. Each of the first set of the plurality of the containers may be configured to receive the first selection of the products and each of the second set of the plurality of the containers configured to receive the second selection of the products based on the received orders. The order dosing filler system may include a plurality of container receptacles configured to receive the first set of the plurality of the containers and the second set of the plurality of the containers, and a container transfer device configured to selectively transfer the first set of the plurality of the containers and the second set of the plurality of the containers from a container holding area to the container receptacles at a container loading station based on the orders. The order dosing filler system may include a container transport assembly including a conveyor. The conveyor may circulate the plurality of the container receptacles among at least the container loading station, the dosing device, and a packing area including a bagger device. The order dosing filler system may include a container sealing device configured to seal to at least a portion of each of the plurality of the containers containing on of the first selection of the products and the second selection of the products such that the products are retained within each of the plurality of the containers. The order dosing filler system may include a container identifier assembly configured to associate at least one identifier with each of the plurality of the containers, the container identifier assembly including at least one of a bar code printer, a seal printer, and a medication identifier printer, and an inspection assembly configured to inspect each of the plurality of the containers, the inspection assembly including at least one of a container sorting device and an imaging device.

In one aspect, the subject matter may provide a method of filling an order of a plurality of orders with a dosing filler system. The method may include dispensing, using a dosing device, a first selection of products into a first set of a plurality of containers and a second selection of the products into a second set of the plurality of the containers. Each of the first set of the plurality of the containers may be configured to receive the first selection of the products and each of the second set of the plurality of the containers may be configured to receive the second selection of the products based on the plurality of the orders. The method may include selectively transferring, using a container transfer device, the first set of the plurality of the containers and the second set of the plurality of the containers from a container holding area to a plurality of container receptacles at a container loading station based on the orders. The container transfer device may include a first set of gripper heads and a second set of the gripper heads. The first set of the gripper heads may be configured to grip and to release the first set of the plurality of the containers. The second set of the gripper heads is configured to grip and release the second set of the plurality of the containers. The method may include circulating, using a container transport assembly, the plurality of the container receptacles among at least the container loading station, the dosing device, and a packing area including a bagger device. The method may include sealing, using a container sealing device, at least a portion of each of the plurality of the containers containing the products such that the selections of the products are retained within each of the plurality of the containers. The method may include associating, using a container identifier assembly, an identifier with each of the plurality of the containers, and may include inspecting, using an inspection assembly, at least one of each of the plurality of the containers and each of the plurality of the container receptacles.

The term "based on" or using, as used herein, reflects an open-ended term that can reflect others elements beyond those explicitly recited. Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled.

The embodiments of the present disclosure generally provide for a plurality of circuits or other electrical devices, which can be used in units, modules, systems, and subsystems and the like. All references to such and the functionality provided by each are not intended to be limited to encompassing only what is illustrated and described herein. While particular labels may be assigned to the various circuits or other electrical devices disclosed, such labels are not intended to limit the scope of operation for the circuits and the other electrical devices. Such circuits and other electrical devices may be combined with each other and/or separated in any manner based on the particular type of electrical/operational implementation that is desired. It is recognized that any circuit or other electrical device disclosed herein may include any number of microprocessors, discrete circuit components, integrated circuits, memory devices (e.g., FLASH, random access memory (RAM), read only memory (ROM), electrically programmable read only memory (EPROM), electrically erasable programmable read only memory (EEPROM), or other suitable variants thereof, etc.) and instructions (e.g., software, etc.) which co-act with one another to perform operation(s) disclosed herein. In addition, any one or more than one electric device may be configured to execute a computer-program that is embodied in a computer readable medium that is programmed to perform any number of the functions and features as disclosed. The computer readable medium may be non-transitory or in any form readable by a machine or electrical component.

At least some portions of the present disclosure may be accomplished by using a robot. A robot can be a machine capable of carrying out a complex series of actions automatically. These complex series of actions may include picking up, orientating, positioning and/or releasing a prescription component, a pill, a container or other structure. The robot may be dedicated to a single series of movements or may be able to execute multiple series of movements. A robot may include a processor that received instructions and then executes instructions to control its movement. In another example, a robot may resemble a human being and replicate certain human movements and functions, may move location, have an articulated arm, have grasping structures that replicate fingers and do not damage containers, and the like.

Methods and systems for pharmacy order processing, including dispensing at least a first selection of products into a first set of containers and a second selection of the products into a second set of the containers and inspecting, sealing, sorting, and packing the containers have been described. Although embodiments of the present disclosure have been described with reference to specific example embodiments, it will be evident that various modifications and changes may be made to these embodiments without departing from the broader spirit and scope of the embodiments of the disclosure. Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion. Although "End" blocks may be shown in the flowcharts, the methods may be performed continuously.

In the foregoing, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more than one steps within a method may be executed in different order (or concurrently) without altering the principles of the present disclosure. Further, although each of the embodiments is described above as having certain features, any one or more than one of those features described with respect to any embodiment of the disclosure can be implemented in and/or combined with features of any of the other embodiments, even if that combination is not explicitly described. In other words, the described embodiments are not mutually exclusive, and permutations of one or more than one embodiments with one another remain within the scope of this disclosure.

Spatial and functional relationships between elements (for example, between modules, circuit elements, semiconductor layers, etc.) are described using various terms, including "connected," "engaged," "coupled," "adjacent," "next to," "on top of" "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more than one intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In this application, including the definitions below, the term 'module' or the term 'controller' may be replaced with the term 'circuit.' The term 'module' may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more than one interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuitry that, in combination with additional processor circuits, executes some or all code from one or more than one modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more than one modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The systems and methods described in this application may be partially or fully implemented by a special purpose computer created by configuring a general purpose computer to execute one or more than one particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more than one operating systems, user applications, background services, background applications, etc.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

None of the elements recited in the claims are intended to be a means-plus-function element within the meaning of 35 U.S.C. § 112(f) unless an element is expressly recited using the phrase "means for," or in the case of a method claim using the phrases "operation for" or "step for."

Embodiments for pharmacy order processing, including dispensing at least a first selection of products into a first set of containers and a second selection of the products into a second set of the containers and inspecting, sealing, sorting, and packing the containers, are described above in detail. The systems and methods of operating such systems are not limited to the specific embodiments described herein, but rather, components of systems and/or steps of the methods may be utilized independently and separately from other components and/or steps described herein. For example, the methods may also be used in combination with other systems and environments and are not limited to the environments as described herein. Rather, the embodiments can be implemented and utilized in connection with many other applications.

In this specification and the claims, reference is made to a number of terms, which shall be defined to have the following meanings:

The singular forms "a", "an", and "the" include plural references unless the context clearly dictates otherwise.

"Optional" or "optionally" means that the subsequently described event or circumstance may or may not occur, and that the description includes instances where the event occurs and instances where it does not.

The term "non-transitory computer-readable media" is intended to be representative of any tangible computer-based device implemented in any method or technology for short-term and long-term storage of information, such as, computer-readable instructions, data structures, program modules and sub-modules, or other data in any device. Therefore, the methods described herein may be encoded as executable instructions embodied in a tangible, non-transitory, computer readable medium, including, without limitation, a storage device and/or a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, cd-roms, dvds, and any other digital source such as a network or the internet, as well as yet to be developed digital means, with the sole exception being a transitory, propagating signal.

The terms "software" and "firmware" are interchangeable, and include any computer program stored in memory for execution by devices that include, without limitation, mobile devices, clusters, personal computers, workstations, clients, and servers.

The term "computer" and related terms, e.g., "computing device", are not limited to integrated circuits referred to in the art as a computer, but broadly refers to a microcontroller, a microcomputer, a programmable logic controller (plc), an application specific integrated circuit, and other programmable circuits, and these terms are used interchangeably herein.

Computer systems are described, and such computer systems include a processor and a memory. However, any processor in a computer device referred to may also refer to one or more processors wherein the processor may be in one computing device or a plurality of computing devices acting in parallel, such as in a cloud computing environment. Additionally, any memory in a computer device referred to may also refer to one or more memories, wherein the memories may be in one computing device or a plurality of computing devices acting in parallel.

A processor may include any programmable system including systems using micro-controllers, reduced instruction set circuits (risc), application specific integrated circuits (asics), logic circuits, and any other circuit or processor capable of executing the functions described herein. The above examples are example only, and are thus not intended to limit in any way the definition and/or meaning of the term "processor." The term "database" may refer to either a body of data, a relational database management system (rdbms), or to both. A database may include any collection of data including hierarchical databases, relational databases, flat file databases, object-relational databases, object oriented databases, and any other structured collection of records or data that is stored in a computer system. The above are only examples, and thus are not intended to limit in any way the definition and/or meaning of the term database. Examples of rdbms's include, but are not limited to including, Oracle® Database, Mysql, IBM® Db2, Microsoft® Sql Server, Sybase®, and Postgresql. However, any database may be used that enables the systems and methods described herein. (oracle is a registered trademark of Oracle Corporation, Redwood Shores, Calif.; IBM is a registered trademark of International Business Machines Corporation, Armonk, new York; Microsoft is a registered trademark of Microsoft Corporation, Redmond, Wash.; and Sybase is a registered trademark of Sybase, Dublin, Calif.)

In some embodiments, a computer program is embodied on a computer readable medium. In other embodiments, the system is executed on a single computer system, without requiring a connection to a server computer. In still other embodiments, the system is run in a Windows® environment (windows is a registered trademark of Microsoft corporation, Redmond, Wash.). In yet another embodiment, the system is run on a mainframe environment and a Unix® server environment (Unix is a registered trademark of x/open company limited located in reading, Berkshire, United Kingdom). The application is flexible and designed to run in various different environments without compromising any major functionality. In some embodiments, the system includes multiple components distributed among a plurality of computing devices. One or more components may be in the form of computer-executable instructions embodied in a computer-readable medium.

Approximating language, as used herein throughout the specification and claims, may be applied to modify any quantitative representation that could permissibly vary without resulting in a change in the basic function to which it is related. Accordingly, a value modified by a term or terms, such as "about" and "substantially", are not to be limited to the precise value specified. In at least some instances, the approximating language may correspond to the precision of an instrument for measuring the value. Here and throughout the specification and claims, range limitations may be combined and/or interchanged; such ranges are identified and include all the sub-ranges contained therein unless context or language indicates otherwise.

The inventive subject matter may be represented in a variety of different embodiments of which there are many possible permutations. Although specific features of various embodiments of the invention may be shown in some drawings and not in others, this is for convenience only. In accordance with the principles of the invention, any feature of a drawing may be referenced and/or claimed in combination with any feature of any other drawing. This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The above detailed description is intended to be illustrative, and not restrictive. The scope of the disclosure should, therefore, be determined with references to the appended claims, along with the full scope of equivalents to which such claims are entitled.

What is claimed is:

1. An order dosing filler system comprising:
an order processing device configured to receive pharmaceutical orders including orders for drugs used in multi-drug regimens, wherein each of the multi-drug regimens has a plurality of scheduled dosing events;
a container transport system;
a container transfer device configured to transfer containers to the container transport system, and the container transport system is configured to transport the containers to a dosing device, a container sealing device, a container identifier assembly, and an inspection assembly, wherein:
the dosing device is configured to communicate with the order processing device and configured to dispense drugs for scheduled dosing times into the containers based on the received pharmaceutical orders, wherein each of the containers corresponds to a respective one of the plurality of scheduled dosing events, and the container transport system is configured to transport the containers with the dispensed drugs to the container sealing device;
the container sealing device is configured to seal to the plurality of the containers with the dispensed drugs, wherein each container retains one or more drugs for one of the multi-drug regimens providing a dosage unit container corresponding to one of the plurality of scheduled dosing events for one of the multi-drug regimens;
the container identifier assembly is configured to identify the dosage unit containers based on the received pharmaceutical order; and
the inspection assembly is configured to inspect each of the dosage unit containers, wherein the inspection assembly includes a first container sorting device configured to at least one of: rotate each of the plurality of the containers containing one of the first selection of the products and the second selection of the products before sealing the respective container; and divert at least one of the plurality of the containers to a separate staging area; and
wherein a second container sorting device is configured to rotate and divert at least one of the plurality of the sealed containers to the staging area; and a second imaging device is configured to image each of the plurality of the containers to determine if the container is sealed and to verify a machine-readable identifier associated with each of the plurality of the containers, wherein the second imaging device includes at least one of a scanner and a machine-readable identifier reader.

2. The order dosing filler system of claim 1, wherein the container transfer device includes heads configured to grip and release the containers.

3. The order dosing filler system of claim 1, wherein the container transfer device includes a first set of containers having a first size and a second set of containers having a second size different from the first size, wherein the container transfer device is configured to transport one of the first set of containers or one of the second set of containers to the container transport system based on received pharmaceutical orders.

4. The order dosing filler system of claim 1, wherein each container includes a rigid or semi-rigid container configured to maintain a cup-shaped form on the container transfer device.

5. The order dosing filler system of claim 1, further comprising a package device configured to package the sealed containers for delivery.

6. The order dosing filler system of claim 1, wherein the container sealing device is configured to seal induction liners on the package as the package travels through an inductive tunnel.

7. The order dosing filler system of claim 1, wherein the container identifier assembly includes a machine-readable printer configured to associate the machine-readable identifier with each of the plurality of the containers.

8. The order dosing filler system of claim 1, wherein the container identifier assembly includes a seal printer configured to associate a timestamp with a seal of each of the plurality of the containers.

9. The order dosing filler system of claim 1, wherein the container identifier assembly includes a medication identifier printer configured to associate a list of one of the first selection of the products and the second selection of the products on each of the plurality of the containers based on the received orders associated with each of the plurality of the containers.

10. The order dosing filler system of claim 1, wherein the inspection assembly includes a first imaging device configured to image an interior of each of the plurality of the containers to determine if one of the first selection of the products and the second selection of the products is present in each of the plurality of the containers.

11. The order dosing filler system of claim 1, wherein the container transport system includes at least one conveyor for transporting the containers to the dosing device, the container sealing device, the container identifier assembly, and the inspection assembly.

12. The order dosing filler system of claim 11, wherein the container transport system includes:
a plurality of pucks attached to the conveyor, wherein individual ones of the plurality of pucks are configured to receive and hold individual ones of the plurality of containers on the conveyor; or
an intelligent conveyor system with electronic movement control.

13. The order dosing filler system of claim 1, wherein the container transport system includes a structure configured to rotate about a vertical axis, wherein the structure has a surface upon which a number of the plurality of containers may be positioned and transported as the structure rotates about the vertical axis, wherein a container loading device, the dosing device, the container sealing device, the container identifier assembly, the inspection assembly and a container unload device are positioned around the structure such that rotation of the structure transports the containers to the dosing device, the container sealing device, the container identifier assembly, the inspection assembly, and the container unload device.

14. A method of filling an order of a plurality of orders with a dosing filler system, the method including:
receiving pharmaceutical orders including order for drugs used in multi-drug regimens using an order processing device, wherein each of the multi-drug regimen has a plurality of scheduled dosing events;
transferring containers to a container transport system;
transporting containers to a dosing device using the container transport system, using the dosing device to dispense drugs for scheduled dosing events into the containers based on the received pharmaceutical orders, wherein each of the containers corresponds to a respective one of the plurality of scheduled dosing events;

transporting, using the container transport system, the containers with the dispensed drugs to the container sealing device, and using the container sealing device to seal the plurality of the containers with the dispensed drugs, wherein each container retains one or more drugs for one of the multi-drug regimens providing a dosage unit container corresponding to one of the plurality of scheduled dosing events for one of the multi-drug regimens;

transporting, using the container transport system, the dosage unit containers to the container identifier assembly, and using the container identifier assembly to identify the dosage unit containers based on the received pharmaceutical order;

transporting, using the container transport system, the dosage unit containers to the inspection assembly, and using the inspection assembly to inspect each of the dosage unit containers, wherein the inspection assembly includes a first container sorting device configured to at least one of: rotate each of the plurality of the containers containing one of the first selection of the products and the second selection of the products before sealing the respective container; and divert at least one of the plurality of the containers to a separate staging area;

rotating and diverting at least one of the plurality of the sealed containers to the staging area, using a second container sorting device; and imaging each of the plurality of the containers to determine if the container is sealed and to verify a machine-readable identifier associated with each of the plurality of the containers, using a second imaging device including at least one of a scanner and a machine-readable identifier reader.

15. The method of claim 14, further comprising packaging the dosage unit containers for delivery.

16. The method of claim 14, wherein each container constructed using a rigid or semi-rigid material configured to maintain a cup-shaped form on the container transfer device, and each dosage unit container includes an induction liner providing a hermetic seal that is tamper evident.

17. A drug package used in a multi-drug regimen having a plurality of scheduled dosing events, the drug package including a plurality of dosage unit containers corresponding to the plurality of scheduled dosing events for the multi-drug regimen, each of the plurality of dosage unit containers containing one or more types of drugs for the multi-drug regimen, and each of the plurality of dosage unit containers being formed from a material to maintain a cup shape in an ambient environment and having an induction liner providing a hermetic seal that is tamper evident, each of the dosage unit containers being labeled with a corresponding one of the plurality of dosing times, and a name and a dosage for each of the one more types of drugs contained with the dosage unit container; and the plurality of dosage unit containers being adapted for transport via a container transfer device transferring containers to a container transport system configured to transport the containers to an order dosing filler system comprising at least:

a dosing device configured to communicate with the order processing device and configured to dispense drugs for scheduled dosing times into the containers based on the received pharmaceutical orders, wherein each of the containers corresponds to a respective one of the plurality of scheduled dosing events, and the container transport system is configured to transport the containers with the dispensed drugs to the container sealing device;

a container sealing device configured to seal to the plurality of the containers with the dispensed drugs, wherein each container retains one or more drugs for one of the multi-drug regimens providing a dosage unit container corresponding to one of the plurality of scheduled dosing events for one of the multi-drug regimens;

a container identifier assembly configured to identify the dosage unit containers based on a received pharmaceutical order;

an inspection assembly configured to inspect each of the dosage unit containers, wherein the inspection assembly includes a first container sorting device configured to at least one of: rotate each of the plurality of the containers containing one of the first selection of the products and the second selection of the products before sealing the respective container; and divert at least one of the plurality of the containers to a separate staging area;

a second container sorting device configured to rotate and divert at least one of the plurality of the sealed containers to the staging area; and a second imaging device configured to image each of the plurality of the containers to determine if the container is sealed and to verify a machine-readable identifier associated with each of the plurality of the containers, wherein the second imaging device includes at least one of a scanner and a machine-readable identifier reader.

18. The drug package of claim 17, wherein each of the dosage unit containers is labeled with a timestamp indicative of a seal time.

19. The drug package of claim 17, wherein the plurality of dosage unit containers is adapted for grip and release by one or more heads of the container transfer device for purposes of transport.

20. The drug package of claim 17, wherein one of the plurality of dosage unit containers is adapted for accommodation by a receptacle of the container transfer device; and wherein the receptacle is sized and shaped to receive a bottom portion or base of the one of the plurality of dosage unit containers.

* * * * *